US009797020B1

(12) United States Patent
Johnson

(10) Patent No.: US 9,797,020 B1
(45) Date of Patent: Oct. 24, 2017

(54) ASSAY FOR THE DETECTION OF AVIAN LEUKOSIS/SARCOMA VIRUSES (ALSV)-INDUCED CANCER OR INFECTION IN DNA FROM HUMAN AND ANIMAL BIOLOGICAL SPECIMENS

(71) Applicant: Eric S. Johnson, Little Rock, AR (US)

(72) Inventor: Eric S. Johnson, Little Rock, AR (US)

( * ) Notice: Subject to any disclaimer, the term of this patent is extended or adjusted under 35 U.S.C. 154(b) by 0 days.

(21) Appl. No.: 14/724,445

(22) Filed: May 28, 2015

Related U.S. Application Data

(60) Provisional application No. 62/003,863, filed on May 28, 2014.

(51) Int. Cl.
*C12Q 1/70* (2006.01)

(52) U.S. Cl.
CPC ........ *C12Q 1/702* (2013.01); *C12Q 2600/112* (2013.01)

(58) Field of Classification Search
None
See application file for complete search history.

(56) References Cited

U.S. PATENT DOCUMENTS 6,391,555 B1 5/2002 Johnson

FOREIGN PATENT DOCUMENTS

CN 101886141 B 11/2010

OTHER PUBLICATIONS

Instant SEQ ID No. 1 sequence alignment with Geneseq database access No. ABL59123 by Johnson in 6391555 on May 2002.*
Instant SEQ ID No. 18 sequence alignment with Geneseq database access No. ABL59129 by Johnson in 6391555 on May 2002.*
Instant SEQ ID No. 19 sequence alignment with Geneseq database access No. ABL59286 by Johnson in 6391555 on May 2002.*
Instant SEQ ID No. 20 sequence alignment with Geneseq database access No. ABL59281 by Johnson in 6391555 on May 2002.*
Instant SEQ ID No. 21 sequence alignment with Geneseq database access No. ABL59283 by Johnson in 6391555 on May 2002.*
Smith et al. (Virus Research. 1998; 54: 87-98).*
Garcia et al., Development and application of reverse transcriptase nested polymerase chain reaction test for the detection of exogenous avian leukosis virus. Avian Dis. Jan.-Mar. 2003; 47(1):41-53.
Davidson et al., Molecular indications for in vivo integration of the avian leukosis virus, subgroup J-long terminal repeat into the Marek's disease virus in experimentally dually-infected chickens. Virus Genes. Mar. 2002; 24(2):173-80.
Lupani et al., Molecular and biological characterization of a naturally occurring recombinant subgroup B avian leukosis virus with a subgroup J-like long terminal repeat. Avian Dis. Dec. 2006; 50(4):572-8.
Silva et al., Development of a polymerase chain reaction to differentiate avian leucosis virus (ALV) subgroups: detection of an ALV contaminant in commercial Marek's disease vaccines. Avian Dis. Sep. 2007; 51(3):663-7.
Silva et al. Hypervariability in the envelope genes of subgroup J avian leukosis viruses obtained from different farms in the United States. Virology. Jun. 20, 2000;272(1):106-11.
Smith et al. Observation on an enzyme-linked immunosorbent assay for the detection of antibodies against avian leukosis-sarcoma viruses. Avian Dis 1986; 30: 488-4493.
Smith et al. Detection of avian leukosis virus subgroup j using the polymerase chain reaction. Avian Dis 1998; 42: 375-380.
Smith et al. Development and application of polymerase chain reaction (PCR) tests for the detection of subgroup J avian leukosis virus. Virus Res 1998; 54: 87-98.
Chen and Barker. Nucleotide sequences of the retroviral long terminal repeats and their adjacent regions. Nucleic Acids Res. Feb. 24, 1984;12(4):1767-78.
Smith et al., An Enzyme-Linked Immunosorbent Assay for Detecting Avian Leukosis-Sarcoma Viruses. Avian Diseases, vol. 23, No. 3 (Jul.-Sep. 1979), pp. 698-707.

* cited by examiner

*Primary Examiner* — Shanon A Foley
(74) *Attorney, Agent, or Firm* — Garvey, Smith & Nehrbass, Patent Attorneys, LLC; Seth M. Nehrbass; Mackenzie D. Rodriguez

(57) ABSTRACT

A method of testing a subject for a propensity to develop, diagnose, or treat ALSV-induced infection or cancer, comprising the steps of obtaining a cell, tissue, or fluid sample from the subject, processing the sample to isolate DNA from the sample, and examining the DNA isolated from the sample to detect the presence of the ALSV LTR. Preferably, the DNA is examined using a PCR-based assay with at least one primer set or any combination of the individual primers in first round or second round reactions from the group consisting of: J1F (SEQ ID NO: 22)/J1R (SEQ ID NO: 24), J1F (SEQ ID NO: 22)/J2R (SEQ ID NO: 25), J2F (SEQ ID NO: 23)/J1R (SEQ ID NO: 24), J2F (SEQ ID NO: 23)/J2R (SEQ ID NO: 25), J1F (SEQ ID NO: 22)/J3R (SEQ ID NO: 26), AL1D (SEQ ID NO: 1)/ALIVR1 (SEQ ID NO: 21), ALIVF1 (SEQ ID NO: 20)/ALIVR1 (SEQ ID NO: 21), AL1D (SEQ ID NO: 1)/NAL2B (SEQ ID NO: 18), ALIVF1 (SEQ ID NO: 20)/NAL2B (SEQ ID NO: 18), AL1D (SEQ ID NO: 1)/ALXB (SEQ ID NO: 19).

26 Claims, 8 Drawing Sheets

Figure 1:
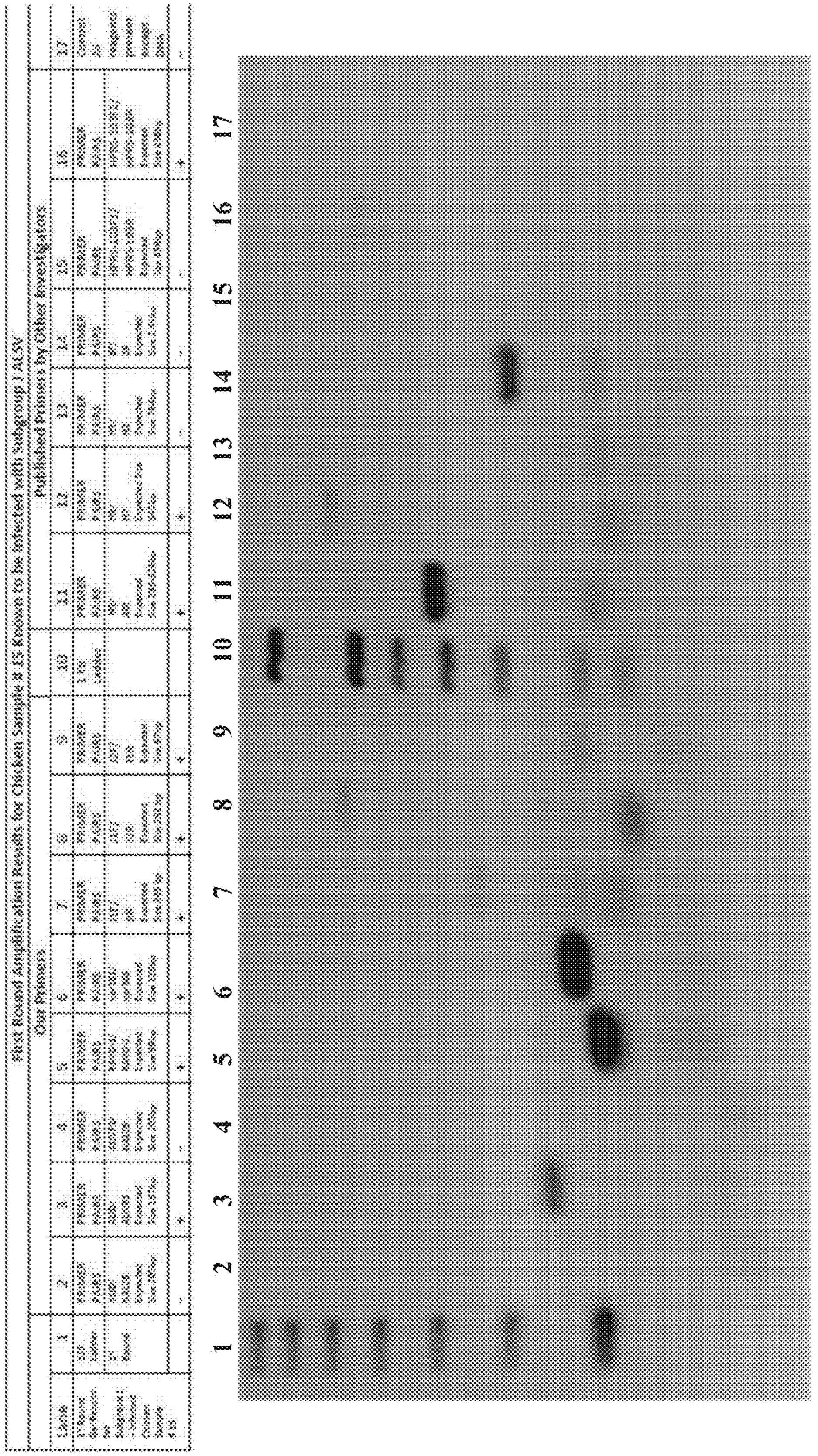

| First Round Amplification Results for DNA from Paraffin Tumor Block from Poultry Worker # 603 Known to have Died from Cancer | | | | | | | | | | | | | | | | | |
|---|---|---|---|---|---|---|---|---|---|---|---|---|---|---|---|---|---|
| | | Our Primers | | | | | | | | | Published Primers by Other Investigators | | | | | | |
| Lane | 1 | 2 | 3 | 4 | 5 | 6 | 7 | 8 | 9 | 10 | 11 | 12 | 13 | 14 | 15 | 16 | 17 |
| 1st Round Gel Results for Poultry Worker Subject # 603 | [illegible] Ladder [illegible] Round | PRIMER PAIRS [illegible] Expected Size [illegible] | PRIMER PAIRS [illegible] Expected Size [illegible] | PRIMER PAIRS [illegible] Expected Size [illegible] | PRIMER PAIRS [illegible] Expected Size [illegible] | PRIMER PAIRS [illegible] Expected Size [illegible] | PRIMER PAIRS [illegible] Expected Size [illegible] | PRIMER PAIRS [illegible] Expected Size [illegible] | PRIMER PAIRS [illegible] Expected Size [illegible] | 1 kb Ladder | PRIMER PAIRS [illegible] Expected Size [illegible] | PRIMER PAIRS [illegible] Expected Size [illegible] | PRIMER PAIRS [illegible] Expected Size [illegible] | PRIMER PAIRS [illegible] Expected Size [illegible] | PRIMER PAIRS [illegible] Expected Size [illegible] | PRIMER PAIRS [illegible] Expected Size [illegible] | Control All reagents present except DNA |
| | | - | + | - | + | + | - | - | + | | + | - | | | - | - | - |

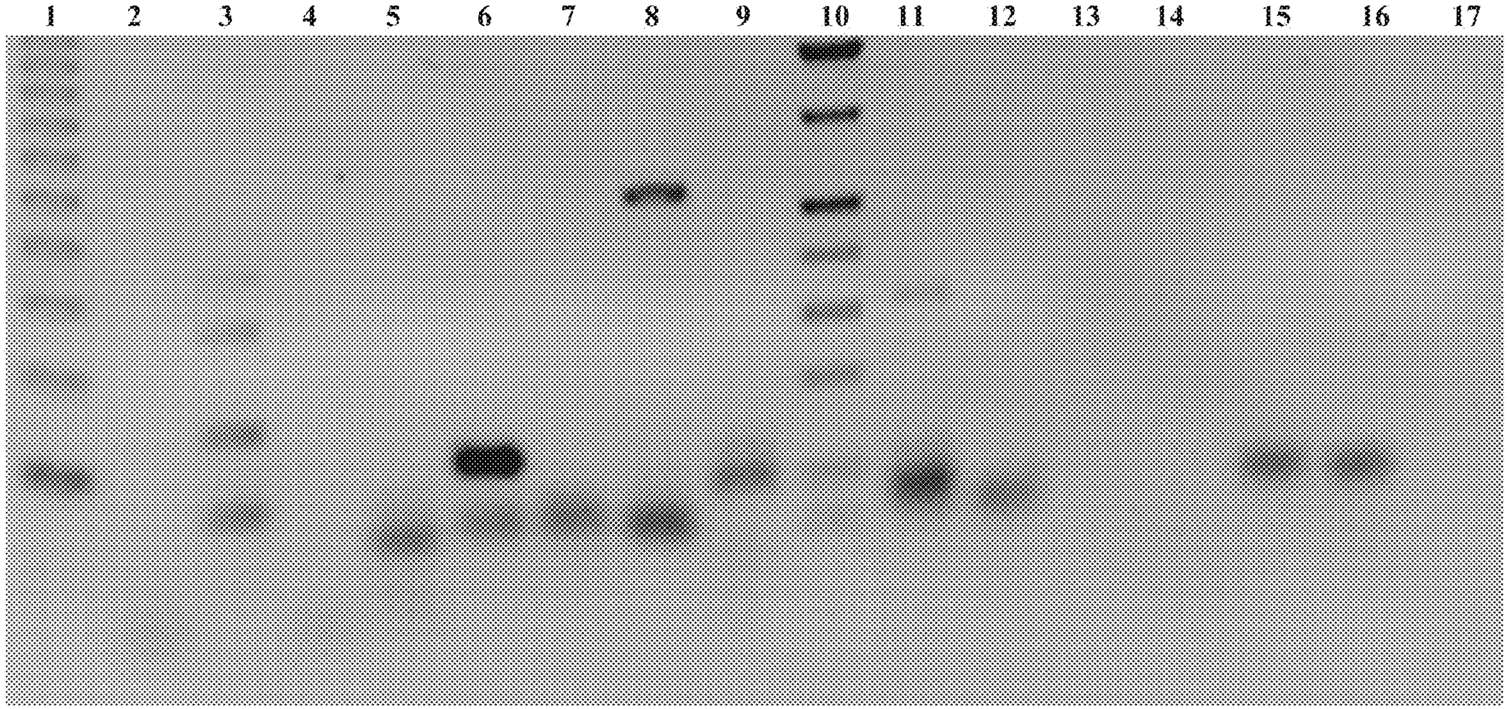

FIG. 3

Amplified DNA sequence submitted to BLAST:

CAGACGGGTCTAACATGGATTGGACGGACTCCTTAGTTCCGCATTGCAGAGATATTGTATTTAAGTGCCTAACCTG
ATACAATAAACGCCATTTTACCTCCCACCACATTGGTGTGCACCTGGGTA

BLAST Result

Avian leukosis virus isolate 98-9 LTR, partial sequence

Sequence ID: gb|AY689486.1| Length: 215

Alignment statistics for match #1

| Score | Expect | Identities | Gaps | Strand |
|---|---|---|---|---|
| 222 bits(120) | 4e-55 | 123/125(98%) | 0/125(0%) | Plus/Plus |

```
Query  1   CAGACGGGTCTAACATGGATTGGACGGACTCCTTAGTTCCGCATTGCAGAGATATTGTAT  60
Sbjct  91  CAGACGGGTCTTACATGGATTGGACGGACTCCTTAGTTCCGCATTRCAGAGATATTGTAT  150

Query  61  TTAAGTGCCTAACCTGATACAATAAACGCCATTTTACCTCCCACCACATTGGTGTGCACC  120
Sbjct  151 TTAAGTGCCTAACCTGATACAATAAACGCCATTTTACCTCCCACCACATTGGTGTGCACC  210

Query  121 TGGGT  125
Sbjct  211 TGGGT  215
```

FIG. 5

Amplified DNA sequence submitted to BLAST:

AGGGAATCAACGGTCCGGCCATCAACCCAGGTGCACACCAATGTGGTGGGAGGTAAAATGGCGTTTATTGTATCA
GGTTAGGCACTTAAATACAATATCTCTGCAATGCGGAACTAAGGAGTCCGTCCAATCCATGTAAGACCCGTCTGTT
GCCTTCCTAATAAGGC*ACGATA* -173 bp in length

BLAST Result

Avian leukosis virus isolate UD2 envelope precursor protein (env) gene, complete cds; and 3'LTR long terminal repeat, complete sequence

Sequence ID: gb|AF307949.1|AF307949 Length: 2589

Range 1: 2381 to 2552

Alignment statistics for match #1

| Score | Expect | Identities | Gaps | Strand |
|---|---|---|---|---|
| 302 bits(163) | 8e-79 | 169/172(98%) | 0/172(0%) | Plus/Minus |

```
Query  1    AGGGAATCAACGGTCCGGCCATCAACCCAGGTGCACACCAATGTGGTGGGAGGTAAAATG  60
Sbjct 2552  AGGGAATCGACGGTCCGGCCATCAACCCAGGTGCACACCAATGTGGTGGGAGGTAAAATG  2493

Query  61   GCGTTTATTGTATCAGGTTAGGCACTTAAATACAATATCTCTGCAATGCGGAACTAAGGA  120
Sbjct  2492 GCGTTTATTGTATCAGGTTAGGCACTTAAATACAATATCTCTGTAATGCGGAACTAAGGA  2433

Query  121  GTCCGTCCAATCCATGTAAGACCCGTCTGTTGCCTTCCTAATAAGGCACGAT  172
Sbjct  2432 GTTCGTCCAATCCATGTAAGACCCGTCTGTTGCCTTCCTAATAAGGCACGAT  2381
```

FIG.6

Amplified DNA sequence submitted to BLAST:

ATGAAGCCTTCTGCTTCATTCAGGTGTTCGCAATCGTTAGGGACTCAACGGTCTGTCCATCTACCCAGGTGCACACC
AATGTGGTGAATGGTAAAATGGA – 100 bp in length

BLAST Results

Gallus gallus endogenous virus ALVE-B11 genomic sequence

Sequence ID: gb|KC610517.1| Length: 7250

Related Information

Range 1: 177 to 275

Alignment statistics for match #1

| Score | Expect | Identities | Gaps | Strand |
|---|---|---|---|---|
| 183 bits(99) | 2e-43 | 99/99(100%) | 0/99(0%) | Plus/Minus |

```
Query  1   ATGAAGCCTTCTGCTTCATTCAGGTGTTCGCAATCGTTAGGGACTCAACGGTCTGTCCAT  60
Sbjct  275 ATGAAGCCTTCTGCTTCATTCAGGTGTTCGCAATCGTTAGGGACTCAACGGTCTGTCCAT  216

Query  61  CTACCCAGGTGCACACCAATGTGGTGAATGGTAAAATGG  99
Sbjct  215 CTACCCAGGTGCACACCAATGTGGTGAATGGTAAAATGG  177
```

FIG. 7

Avian leukosis virus strain TW-3593, complete genome

Sequence ID: gb|HM582658.1| Length: 7483

Related Information

Range 1: 177 to 275

Alignment statistics for match #1

| Score | Expect | Identities | Gaps | Strand |
|---|---|---|---|---|
| 183 bits(99) | 2e-43 | 99/99(100%) | 0/99(0%) | Plus/Minus |

```
Query  1   ATGAAGCCTTCTGCTTCATTCAGGTGTTCGCAATCGTTAGGGACTCAACGGTCTGTCCAT  60
Sbjct  275 ATGAAGCCTTCTGCTTCATTCAGGTGTTCGCAATCGTTAGGGACTCAACGGTCTGTCCAT  216

Query  61  CTACCCAGGTGCACACCAATGTGGTGAATGGTAAAATGG  99
Sbjct  215 CTACCCAGGTGCACACCAATGTGGTGAATGGTAAAATGG  177
```

Amplified DNA sequence submitted to BLAST:

GTCAGGGAATCGACGGTCCGGCCATCAACCCAGGTGCACACCAATGTGGTGGGAGGTAAAATGGCGTTTATTGTATCAGG
CTAGGCACTTAAATACAA – 98bp in length.

BLAST Results

Avian leukosis virus isolate SD110503R, complete genome

Sequence ID: gb|KF738251.1|Length: 7708

Related Information

Range 1: 192 to 289

Alignment statistics for match #1

| Score | Expect | Identities | Gaps | Strand |
|---|---|---|---|---|
| 182 bits(98) | 5e-43 | 98/98(100%) | 0/98(0%) | Plus/Minus |

```
Query 1    GTCAGGGAATCGACGGTCCGGCCATCAACCCAGGTGCACACCAATGTGGTGGGAGGTAAA  60
Sbjct 289  GTCAGGGAATCGACGGTCCGGCCATCAACCCAGGTGCACACCAATGTGGTGGGAGGTAAA  230

Query 61   ATGGCGTTTATTGTATCAGGCTAGGCACTTAAATACAA  98
Sbjct 229  ATGGCGTTTATTGTATCAGGCTAGGCACTTAAATACAA  192
```

FIG. 8

ASSAY FOR THE DETECTION OF AVIAN LEUKOSIS/SARCOMA VIRUSES (ALSV)-INDUCED CANCER OR INFECTION IN DNA FROM HUMAN AND ANIMAL BIOLOGICAL SPECIMENS

CROSS-REFERENCE TO RELATED APPLICATIONS

This application claims the benefit of U.S. Provisional Patent Application Ser. No. 62/003,863, filed on 28 May 2014, which is incorporated herein by reference.

Priority of U.S. Provisional Patent Application Ser. No. 62/003,863, filed on 28 May 2014, is hereby claimed.

STATEMENT REGARDING FEDERALLY SPONSORED RESEARCH OR DEVELOPMENT

Not Applicable.

REFERENCE TO A "MICROFICHE APPENDIX"

Not applicable.

BACKGROUND OF THE INVENTION

1. Field of the Invention

The present invention relates to avian leukosis/sarcoma virus (ALSV)-induced cancer or infection. More particularly, the present invention relates to a method for the detection of the propensity to develop ALSV-induced cancer or infection, and a method to diagnose cancer or infection induced by both exogenous and endogenous ALSV.

2. General Background of the Invention

Incorporated herein by reference are U.S. Pat. No. 6,391,555, issued on 21 May 2002; U.S. patent application Ser. No. 09/479,770, filed 7 Jan. 2000 (issued as U.S. Pat. No. 6,391,555 on 21 May 2002); U.S. patent application Ser. No. 08/697,912, filed 30 Aug. 1996; and U.S. Provisional Patent Application Ser. No. 60/115,087, filed 7 Jan. 1999.

The following references are incorporated herein by reference:

Davidson et al., Molecular indications for in vivo integration of the avian leukosis virus, subgroup J-long terminal repeat into the Marek's disease virus in experimentally dually-infected chickens. Virus Genes. 2002 March; 24(2):173-80;

Fadly A M, Witter R L. Oncornaviruses: Leukosis/Sarcoma and reticuloendotheliosis. In J R Glisson, D J Jackwood, J E Pearson, W M Reed, and D E Swayne (Eds). A laboratory manual for the isolation and identification of avian pathogens 4th edition (pp. 185-196), (1998). Kennett Square, Pa.: American Association of Avian Pathologists;

Garcia et al., Development and application of reverse transcriptase nested polymerase chain reaction test for the detection of exogenous avian leukosis virus. Avian Dis. 2003 January-March; 47(1):41-53;

Gao et al., Molecular epidemiology of avian leukosis virus subgroup J in layer flocks in China. J Clin Microbiol. 2012 March; 50(3):953-60; Johnson, Eric S., Lila Overby, and Richard Philpot, "Detection of Antibodies to Avian Leukosis/Sarcoma Viruses and Reticuloendotheliosis Viruses in Humans by Western Blot Assay", CANCER DETECTION AND PREVENTION, 19(6):472-486 (1995);

Johnson, Eric S., Lori Nicholson, and David Durack, "Detection of Antibodies to Avian Leukosis/Sarcoma Viruses (ALSV) and Reticuloendotheliosis Viruses (REV) in Humans by ELISA", CANCER DETECTION AND PREVENTION, 19(5):394-404(1995);

Lupani et al., Molecular and biological characterization of a naturally occurring recombinant subgroup B avian leukosis virus with a subgroup J-like long terminal repeat. Avian Dis. 2006 December; 50(4):572-8;

Meng et al., Enhanced inhibition of Avian leukosis virus subgroup J replication by multi-target miRNAs. Virol J. 2011 Dec. 22; 8:556;

Payne L N, Fadly A M. Leukosis/Sarcoma group. In: B W Calnek, H J Barnes, C W Beard, L R McDougald, Y M Saif (Eds). Diseases of Poultry, 10th Ed.; pp 414-466. Iowa State University Press, Ames, Iowa;

Silva et al., Development of a polymerase chain reaction to differentiate avian leucosis virus (ALV) subgroups: detection of an ALV contaminant in commercial Marek's disease vaccines. Avian Dis. 2007 September; 51(3):663-7.

U.S. Pat. Nos. 5,710,010; 5,716,832; 5,703,055; 5,672,485, 5,591,624; 5,258,299; 5,049,502; 5,028,540; 6,096,534; 6,146,641; 6,794,188; 7,507,527; 7,625,742; H001065; U.S. Patent Application Publication No. 2003/0203868; 2014/0147834; PCT Publication No. WO00/04921; WO02013/189003; Foreign Publication No. CN1437023A; CN101886141B; CN101899465A; CN102304181 A; CN102876675A; CN102943127A; CN103074447A; CN103555714A; CN103614329A; CN103937833A; and all references mentioned herein.

BRIEF SUMMARY OF THE INVENTION

The method of the present invention solves the problems of detecting, diagnosing, and treating ALSV-induced cancer or infection in a simple and straightforward manner. What is provided is a method of 1) testing a subject for a propensity to develop, 2) diagnosing, and 3) treating ALSV induced cancer or infection, comprising obtaining a sample of cells or tissue from the subject, processing the cell/tissue sample to isolate DNA from the sample, and examining the DNA isolated from the sample to detect the presence of the ALSV LTR. This sample can be, but is not limited to, cells, tissue, or a tumor. The DNA can be examined using a PCR-based assay with the aid of at least one primer set or any combination of the individual primers in first round or second round reactions from the group comprising of: AL1D (SEQ ID NO: 1)/AL2B (SEQ ID NO: 2), nprA181 (SEQ ID NO: 3)/nprA308 (SEQ ID NO: 4), nprA271 (SEQ ID NO: 5)/AL2B (SEQ ID NO: 2), RAVO-1 (SEQ ID NO: 6)/RAVO-2 (SEQ ID NO: 7), AL1D (SEQ ID NO: 1)/A-Au (SEQ ID NO: 13), S-Au (SEQ ID NO: 12)/A-Au (SEQ ID NO: 13), and nprA271 (SEQ ID NO: 5)/AAu (SEQ ID NO: 13), Sn271J (SEQ ID NO: 14)/A-AuJ (SEQ ID NO: 15). The following primers are additionally added to be used in the assay in any combination, as they expand the capacity of the assay to detect specifically ALSV subtypes of the subgroup J group in addition to the other subgroups, and also defective ALSV: J1F (SEQ ID NO: 22)/J1R (SEQ ID NO: 24), J1F (SEQ ID NO: 22)/J2R (SEQ ID NO: 25), J2F (SEQ ID NO: 23)/J1R (SEQ ID NO: 24), J2F (SEQ ID NO: 23)/J2R (SEQ ID NO: 25), J1F (SEQ ID NO: 22)/J3R (SEQ ID NO: 26), AL1D (SEQ ID NO: 1)/ALIVR1 (SEQ ID NO: 21), ALIVF1 (SEQ ID NO: 20)/ALIVR1 (SEQ ID NO: 21), AL1D (SEQ ID NO: 1)/NAL2B (SEQ ID NO: 18), ALIVF1 (SEQ ID NO: 20)/NAL2B (SEQ ID NO: 18), AL1D (SEQ ID NO: 1)/ALXB (SEQ ID NO: 19).

Incorporated herein by reference is the manuscript titled "A comparison of the performance of a new PCR assay and new primers for amplifying ALSV Subgroup J-specific infections and other ALSV subgroups with published PCR assays and primers" and submitted with U.S. Provisional Patent Application Ser. No. 62/003,863.

BRIEF DESCRIPTION OF THE SEVERAL VIEWS OF THE DRAWINGS AND SEQUENCE LISTING

Figure 2:
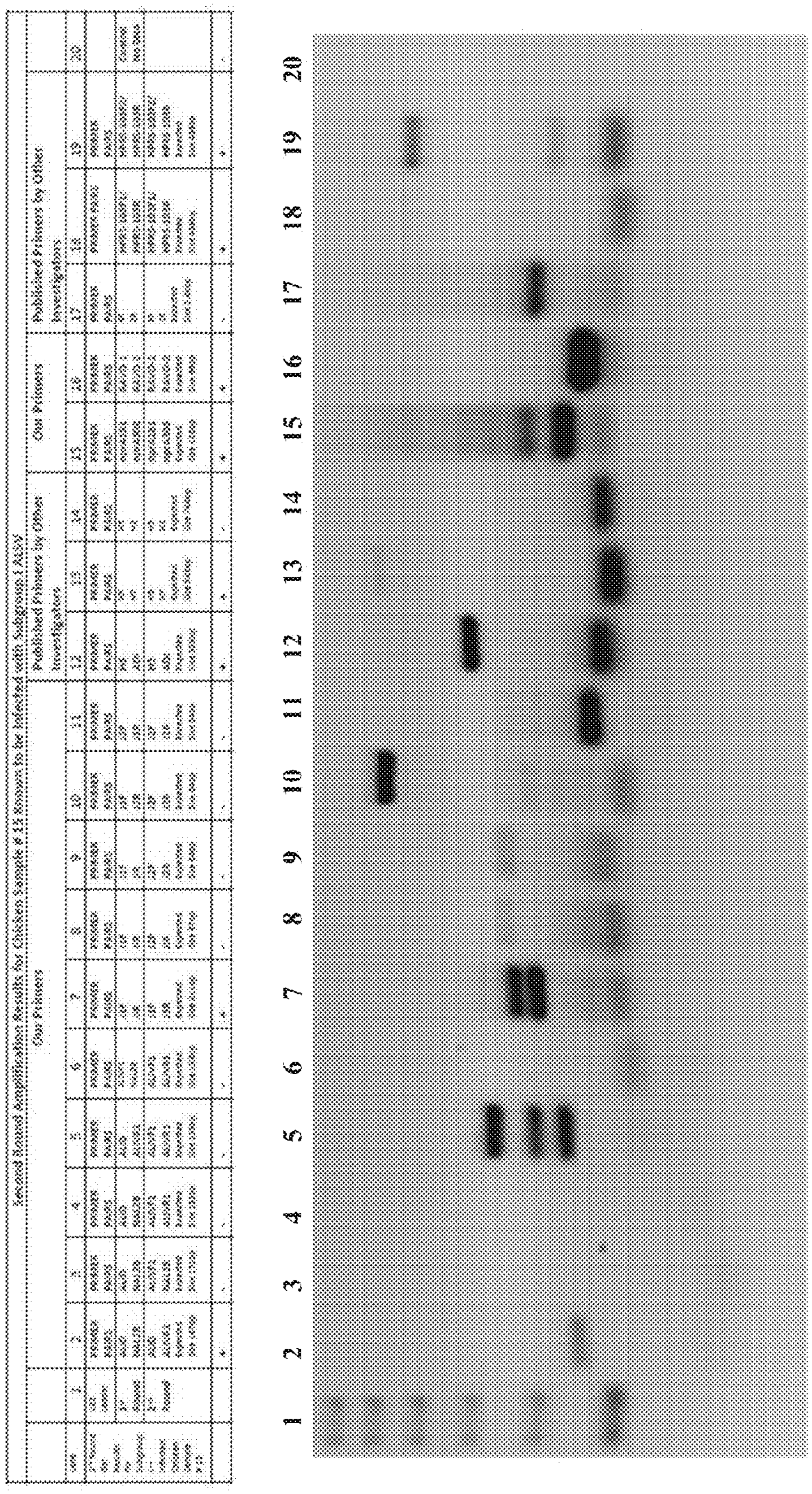
Figure 4:
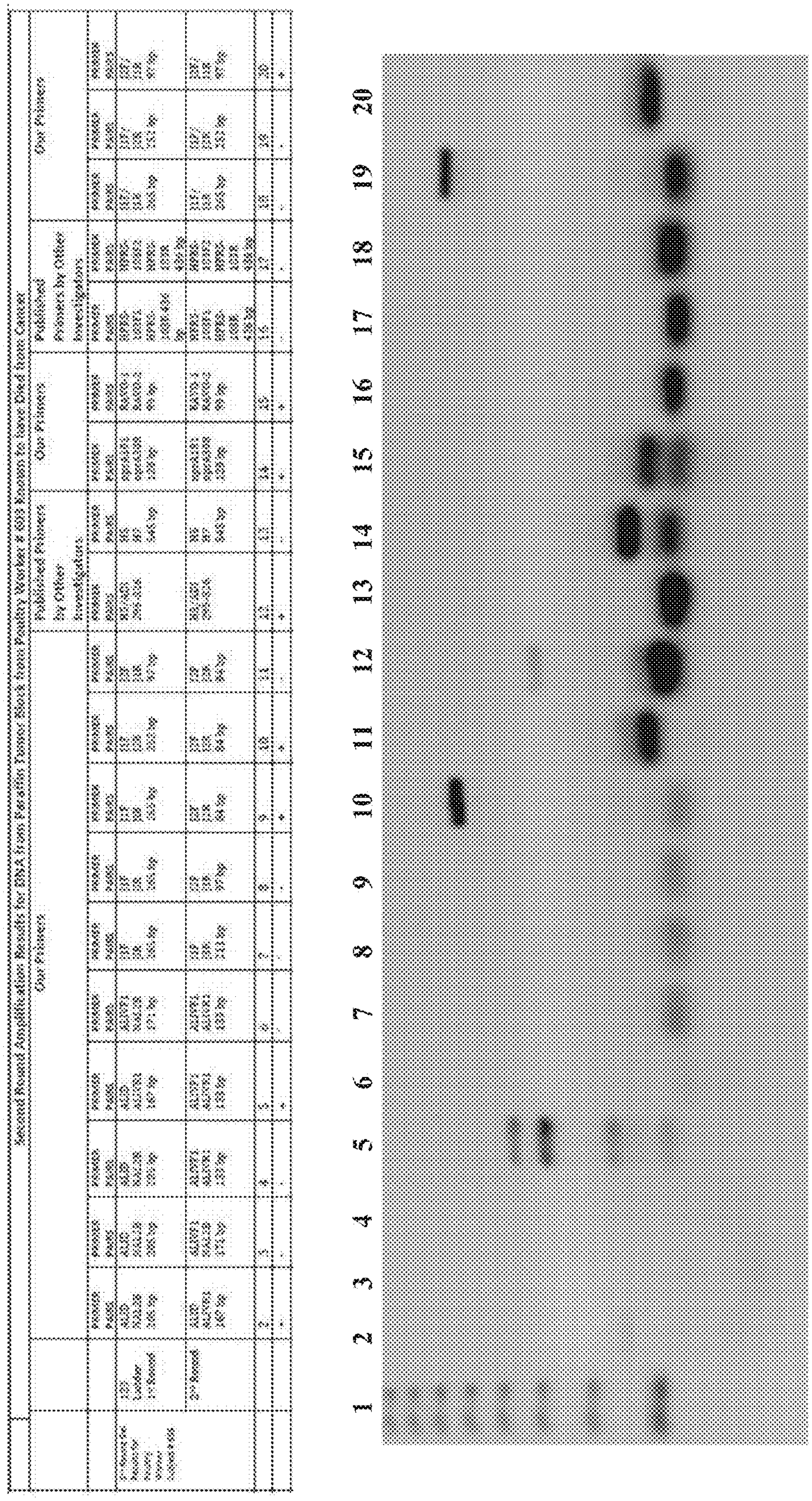

For a further understanding of the nature, objects, and advantages of the present invention, reference should be had to the following detailed description, read in conjunction with the following drawings, wherein:

FIG. 1 shows the first round amplification PCR results for Chicken Sample #15 known to be infected with Subgroup J ALSV; Lane 1 corresponds to 123 Ladder; Lane 2 corresponds to Primer Pairs ALID (SEQ ID NO: 1)/NALD2B (SEQ ID: 18); Lane 3 corresponds to Primer Pairs ALID (SEQ ID NO: 1)/ALIVR1 (SEQ ID NO: 21); Lane 4 corresponds to Primer Pairs ALIVF1 (SEQ ID NO:20)/NAL2B (SEQ ID NO: 18); Lane 5 corresponds to Primer Pairs RAVO-1 (SEQ ID NO:6)/RAVO-2 (SEQ ID NO: 7) (previously published primer pairs found in U.S. Pat. No. 6,391,555 by Johnson); Lane 6 corresponds to Primer Pairs npr181 (SEQ ID NO:3/npr308 (SEQ ID NO: 4) (previously published primer pairs found in U.S. Pat. No. 6,391,555 by Johnson); Lane 7 corresponds to Primer Pairs J1F (SEQ ID NO: 22)/J1R (SEQ ID NO: 24); Lane 8 corresponds to Primer Pairs J1F (SEQ ID NO: 22)/J2R (SEQ ID NO: 25); Lane 9 corresponds to Primer Pairs J2F (SEQ ID NO: 23)/J1R (SEQ ID NO: 24); Lane 10 corresponds to 1 kb ladder; Lanes 11-16 correspond to published primer pairs by other investigators; Lane 17 corresponds to Control (All reagents present except DNA):

FIG. 2 shows the second round amplification PCR results for Chicken Sample #15 known to be infected with Subgroup J ALSV; Lane 1 corresponds to 123 Ladder for the 1$^{st}$ Round and the 2$^{nd}$ Round; Lane 2 corresponds to Primer Pairs ALID (SEQ ID NO: 1)/NAL2B (SEQ ID NO: 18) for the 1$^{st}$ Round and ALID (SEQ ID NO: 1) ALIVR1 (SEQ ID NO: 21) for the 2$^{nd}$ Round; Lane 3 corresponds to Primer Pairs ALID (SEQ ID NO: 1)/NAL2B (SEQ ID NO: 18) for the 1$^{st}$ Round and ALIVF1 (SEQ ID NO: 20)/NAL2B (SEQ ID NO: 18) for the 2$^{nd}$ Round; Lane 4 corresponds to Primer Pairs ALID (SEQ ID NO: 1)/NAL2B (SEQ ID NO: 18) for the 1$^{st}$ Round and ALIVF1 (SEQ ID NO: 20)/ALIVR1 (SEQ ID NO: 21) for the 2$^{nd}$ Round; Lane 5 corresponds to Primer Pairs ALID (SEQ ID NO: 1) ALIVR1 (SEQ ID NO: 21) for the 1$^{st}$ Round and ALIVF1 (SEQ ID NO: 20)/ALIVR1 (SEQ ID NO: 21) for the 2$^{nd}$ Round; Lane 6 corresponds to Primer Pairs ALIVF1 (SEQ ID NO: 20)/NAL2B (SEQ ID NO: 18) for the 1$^{st}$ Round and ALIVF1 (SEQ ID NO: 20)/ALIVR1 (SEQ ID NO: 21) for the 2$^{nd}$ Round; Lane 7 corresponds to J1F (SEQ ID NO: 22)/J1R (SEQ ID NO:24) for the 1$^{st}$ Round and J1F (SEQ ID NO: 22)/J3R (SEQ ID NO:26) for the 2$^{nd}$ Round; Lane 8 corresponds to Primer Pairs J1F (SEQ ID NO: 22)/J1R (SEQ ID NO:24) for the 1$^{st}$ Round and J2F (SEQ ID NO:23)/J1R (SEQ ID NO: 24) for the 2$^{nd}$ Round; Lane 9 corresponds to Primer Pairs J1F (SEQ ID NO: 22)/J1R (SEQ ID NO:24) for the 1$^{st}$ Round and J2F (SEQ ID NO: 23)/J2R (SEQ ID NO: 25) for the 2$^{nd}$ Round: Lane 10 corresponds to Primer Pairs J1F (SEQ ID NO: 22)/J2R (SEQ ID NO: 25) for the 1$^{st}$ Round and J2F (SEQ ID NO: 23)/J2R (SEQ ID NO: 25); Lane 11 corresponds to Primer Pairs J2F (SEQ ID NO:23)/J1R (SEQ ID NO: 24) for the 1$^{st}$ Round and J2F (SEQ ID NO: 23)/J2R (SEQ ID NO:25) for the 2$^{nd}$ Round; Lanes 12-14 correspond to published primer pairs for other investigators; Lane 15 corresponds to Primer Pairs nprA181 (SEQ ID NO: 3)/nprA308 (SEQ ID NO: 4) (previously published primer pairs found in U.S. Pat. No. 6,391,555 by Johnson) for the 1$^{st}$ Round and nprA181 (SEQ ID NO: 3)/nprA308 (SEQ ID NO: 4) (previously published primer pairs found in U.S. Pat. No. 6,391,555 by Johnson) for the 2$^{nd}$ Round; Lane 16 corresponds to Primer Pairs RAVO-1 (SEQ ID NO: 6)/RAVO-2 (SEQ ID NO: 7) (previously published primer pairs found in U.S. Pat. No. 6,391,555 by Johnson) for the 1$^{st}$ Round and RAVO-1 (SEQ ID NO:6)/RAVO-2 (SEQ ID NO: 7) (previously published primer pairs found in U.S. Pat. No. 6,391,555 by Johnson) for the 2$^{nd}$ Round: Lanes 17-19 correspond to published primer pairs for other investigators; Lane 20 corresponds to Control (All reagents present except DNA):

FIG. 3 shows the first round amplification PCR results for DNA extracted from a paraffin tumor block from Poultry Worker #603 known to have died from cancer; Lane 1 corresponds to 123 Ladder; Lane 2 corresponds to Primer Pairs ALID (SEQ ID NO: 1)/NALD2B (SEQ ID: 18); Lane 3 corresponds to Primer Pairs ALID (SEQ ID NO: 1) ALIVR1 (SEQ ID NO:21); Lane 4 corresponds to Primer Pairs ALIVF1 (SEQ ID NO: 20)/NAL2B (SEQ ID NO: 18); Lane 5 corresponds to Primer Pairs RAVO-1 (SEQ ID NO: 6)/RAVO-2 (SEQ ID NO: 7): Lane 6 corresponds to Primer Pairs npr181 (SEQ ID NO: 3)/npr308 (SEQ ID NO: 4); Lane 7 corresponds to Primer Pairs J1F (SEQ ID NO: 22)/J1R (SEQ ID NO: 24); Lane 8 corresponds to Primer Pairs J1F (SEQ ID NO: 22)/J2R (SEQ ID NO: 25); Lane 9 corresponds to Primer Pairs J2F (SEQ ID NO: 23)/JR (SEQ ID NO: 24); Lane 10 corresponds to 1 kb ladder; Lanes 11-16 correspond to published primer pairs by other investigators; Lane 17 corresponds to Control (All reagents present except DNA):

FIG. 4 shows the second round amplification PCR results for DNA extracted from a paraffin tumor block from Poultry Worker #603 known to have died from cancer; Lane 1 corresponds to 123 Ladder for the 1$^{st}$ Round and the 2$^{nd}$ Round; Lane 2 corresponds to Primer Pairs ALID (SEQ ID NO: 1)/NAL2B (SEQ ID NO: 18) for the 1$^{st}$ Round and ALID (SEQ ID NO: 1)/ALIVR1 (SEQ ID NO: 21) for the 2$^{nd}$ Round; Lane 3 corresponds to Primer Pairs ALID (SEQ ID NO: 1) NAL2B (SEQ ID NO: 18) for the 1$^{st}$ Round and ALIVF1 (SEQ ID NO: 20) NAL2B (SEQ ID NO: 18) for the 2$^{nd}$ Round; Lane 4 corresponds to Primer Pairs ALID (SEQ ID NO: 1)/NAL2B (SEQ ID NO: 18) for the 1$^{st}$ Round and ALIVF1 (SEQ ID NO: 20)/ALIVR1 (SEQ ID NO: 21) for the 2$^{nd}$ Round; Lane 5 corresponds to Primer Pairs ALID (SEQ ID NO: 1)/ALIVR1 (SEQ ID NO: 21) for the 1$^{st}$ Round and ALIVF1 (SEQ ID NO: 20)/ALIVR1 (SEQ ID NO: 21) for the 2$^{nd}$ Round; Lane 6 corresponds to Primer Pairs ALIVF1 (SEQ ID NO: 20)/NAL2B (SEQ ID NO: 18) for the 1$^{st}$ Round and ALIVF1 (SEQ ID NO: 20)/ALIVR1 (SEQ ID NO:21) for the 2$^{nd}$ Round; Lane 7 corresponds to J1F (SEQ ID NO: 22)/J1R (SEQ ID NO: 24) for the 1$^{st}$ Round and J1F (SEQ ID NO: 22)/J3R (SEQ ID NO: 26) for the 2$^{nd}$ Round; Lane 8 corresponds to Primer Pairs J1F (SEQ ID NO: 22)/J1R (SEQ ID NO: 24) for the 1$^{st}$ Round and J2F (SEQ ID NO: 23)/J1R (SEQ ID NO: 24) for the 2$^{nd}$ Round; Lane 9 corresponds to Primer Pairs J1F (SEQ ID NO: 22)/J1R (SEQ ID NO: 24) for the 1$^{st}$ Round and J2F (SEQ ID NO:23)/J2R (SEQ ID NO: 25) for the 2$^{nd}$ Round; Lane 10 corresponds to Primer Pairs J1F (SEQ ID NO: 22)/J2R (SEQ ID NO: 25) for the 1st Round and J2F (SEQ ID NO: 23)/J2R (SEQ ID NO: 25); Lane 11 corresponds to Primer Pairs J2F (SEQ ID NO: 23)/J1R (SEQ ID NO: 24) for the 1st Round and J2F (SEQ ID NO: 23)/J2R (SEQ ID NO: 25) for the 2nd Round; Lanes 12-13 correspond to published primer pairs by other investigators; Lane 14 corresponds to Primer Pairs nprA181 (SEQ ID NO: 3)/nprA308 (SEQ ID NO: 4) (previously published primer pairs found in U.S. Pat. No. 6,391,555 by Johnson) for the 1st Round and nprA181 (SEQ ID NO: 3)/nprA308 (SEQ ID NO: 4) (previously published primer pairs found in U.S. Pat. No. 6,391,555 by Johnson) for the 2nd Round: Lane 15 corresponds to Primer Pairs RAVO-1 (SEQ ID NO: 6)/RAVO-2 (SEQ ID NO: 7) (previously published primer pairs found in U.S. Pat. No. 6,391,555 by Johnson) for the 1st Round and RAVO-1 (SEQ ID NO: 6)/RAVO-2 (SEQ ID NO: 7) (previously published primer pairs found in U.S. Pat. No. 6,391,555 by Johnson) for the 2nd Round; Lanes 16-17 correspond to published primer pairs for other investigators; Lane 18 corresponds to Primer Pairs J1F (SEQ ID NO: 22)/J1R (SEQ ID NO: 24) for the 1st Round and J1F (SEQ ID NO: 22)/J1R (SEQ ID NO: 24) for the 2nd Round: Lane 19 corresponds to Primer Pairs J1F (SEQ ID NO:22)/J2R (SEQ ID NO:25) for the 1st Round and J1F (SEQ ID NO: 22)/J2R (SEQ ID NO:25) for the 2nd Round; Lane 20 corresponds to Primer Pairs J2F (SEQ ID NO: 23)/J1R (SEQ ID NO:24) for the 1st Round and J2F (SEQ ID NO: 23)/J1R (SEQ ID NO: 24):

FIG. 5 shows a BLAST result for a segment of ALSV amplified by primer set nprA181 (SEQ ID NO: 3)/nprA308 (SEQ ID NO: 4) (previously published primer pairs found in U.S. Pat. No. 6,391,555 by Johnson) in DNA extracted from chicken tissue known to be infected with subgroup J virus;

FIG. 6 shows a BLAST result for a segment of ALSV amplified by primer set AL1D (SEQ ID NO: 1)/ALIVR1 (SEQ ID NO: 21) in DNA extracted from chicken tissue known to be infected with subgroup J virus;

FIG. 7 shows BLAST results for segments of ALSV amplified by primer set RAVO-1 (SEQ ID NO: 6)/RAVO-2 (SEQ ID NO: 7) (previously published primer pairs found in U.S. Pat. No. 6,391,555 by Johnson) in DNA extracted from chicken tissue known to be infected with subgroup J virus; and FIG. 8 shows a BLAST result for a segment of ALSV amplified by primer set J2F (SEQ ID NO: 23)/J1R (SEQ ID NO: 24) in DNA extracted from human cancer tissue from a poultry worker who died of cancer.

The Sequence Listing contains the one letter code for nucleotide sequence characters, which is hereby incorporated by reference. The symbols and format used for nucleotide sequence data comply with the rules set forth in 37 C.F.R. 1.822. The Sequence Listing attached hereto complies with the rules governing nucleotide and/or amino acid sequence disclosures in patent applications as set forth in 37 C.F.R. §1.821-1.825.

DETAILED DESCRIPTION OF THE INVENTION

In an as-yet unpublished article entitled "Avian leukosis/sarcoma Viruses—A new cause of human cancer?" (a copy of which is attached to U.S. Provisional Patent Application Ser. No. 60/115,087 and is hereby incorporated herein by reference), the inventor discusses the possibility that human cancer could be caused by avian leukosis/sarcoma viruses.

The group of avian leukosis/sarcoma viruses (ALSV) include viruses which are among the most potent carcinogenic agents known.[1] In spite of the fact that it has been known for more than 30 years that they can infect and transform human cells in vitro, and can induce tumors in subhuman primates in vivo,[1] for a very long time no further evidence was presented that they pose a potential cancer risk for humans. Recent epidemiological studies now clearly show that subjects with high exposure to these and other oncogenic viruses of cattle and chickens, have increased risk of cancer.[2-13] Furthermore, there is now clear serologic evidence that humans are exposed to ALSV. 14-16 Our studies have been the only ones to have included a cohort of ALSV exposed workers, and an excess of five cancer types was observed in this group.[2-6, 8, 9]

The method of the present invention uses a PCR-based assay to detect integrated ALSV provirus in ALSV-exposed cancer patients and infected subjects. By detecting integrated ALSV provirus in the human genome using the method of the present invention, ALSV is shown to be a new cause of human cancer. This information is useful for the diagnosis and treatment of ALSV-induced cancer patients and infected subjects. Furthermore, detection of integrated ALSV pro virus in the cells and/or tissues of people who have not yet developed cancer, can help to determine the propensity of that individual developing ALSV-induced cancer in the future. If the ALSV pro virus is detected, the likelihood of developing ALSV-induced cancer is significantly greater than if the ALSV provirus is not detected. In addition, detection of integrated ALSV virus in samples from humans who have already developed tumors can lead to the diagnosis of ALSV-induced cancer. This will greatly facilitate treatment, as the treatment can then be made more specific, and hence more effective.

We previously studied cancer mortality risk in a cohort of 28,900 subjects who were members of a local meat cutters' union in Baltimore, Md.[2-9] The cohort included 2,639 subjects who were employed in poultry slaughtering/processing plants, and 10,841 employed in the meat department of supermarkets, with potential exposure to ALSV. An additional 6,081 members of this cohort were employed in companies outside the meat industry such as soft drinks manufacturing and oyster shucking, and had no known occupational exposure to ALSV (control group). We observed statistically significant excess of cancers in five sites including the lung, liver, colon, esophagus, and hemopoietic/lymphatic systems in the group of ALSV-exposed workers, when compared to this control group of nonmeat workers.[2-6,8,9] These results provide, for the first time, confirmation in an analytic epidemiological study, of the association between cancer in humans and poultry.

Because the ALSV-exposed workers had statistically significant excess of cancers of the lung, liver, colon, esophagus, and hemopoietic/lymphatic systems, tissues samples were taken from the tumors that developed in these sites. Tumor samples from a group of subjects who have one of the highest known human exposure levels to ALSV have an increased risk of carrying the integrated virus. We therefore collected paraffin tumor blocks of this specific group of subjects from the hospitals in which death occurred, and have a total of 64 samples in our possession. We present here, the results of the first five samples we have investigated for the presence of the ALSV long terminal repeat (LTR) and gag gene in these tumor samples.

Sources of Paraffin Blocks

Case# I (No. 1366571) worked in a poultry slaughtering/processing plant for 14 months, and had a death certificate diagnosis of lung cancer as cause of death, at age 50 years.

The hospital pathology report on a bone marrow aspirate of which the paraffin tumor block was prepared, indicated metastatic poorly differentiated carcinoma, with lung or gastrointestinal tract as the possible primary site.

Case #2 (No. 9190300) worked in a poultry slaughtering/processing plant for one month, and died at age 51 years with a death certificate diagnosis of malignant melanoma of skin. The hospital pathology report confirmed the death certificate diagnosis. Case #3 (No. 1832107) worked in a poultry slaughtering/processing plant for three months, and died at age 71 years with a death certificate diagnosis of cancer of the tongue. The hospital pathology report indicated a poorly differentiated squamous cell carcinoma of the tongue.

Case #4 (No. 0731793) worked in a cattle/pig/sheep slaughtering/processing plant which also had an egg-candling facility, for 323 months. Death occurred at age 52 years, with a death certificate diagnosis of lung cancer. The hospital pathology report indicated a moderately differentiated squamous cell carcinoma of the right lung.

Case #5 (No. 1765805) worked in a cattle & pig slaughtering/processing plant for 132 months, and died at age 76 years with a death certificate diagnosis of lung cancer. The hospital pathology reports of both lung biopsy and bronchial washings indicated a moderately differentiated squamous cell carcinoma of the left lung.

DNA was abstracted from a single paraffin block from each subject. To minimize the occurrence of contamination, no plasmid ALSV DNA or DNA from ALSV-positive tumor was handled in the laboratory during the two-week period preceding testing of the first two human DNA samples. For the same reason, no positive control DNA sample (ALSV plasmid DNA or DNA from ALSV-induced chicken tumor) was used concomitantly while these samples were being tested. Primers designed to amplify portions of the ALSV LTR and gag gene were employed.

PCR Results for Subject#1366571

This was the first sample tested which was positive. The testing was done on 9 Feb. 1997. None of the primers amplified a visible product after the first amplification of 35 cycles. On re-amplification of the PCR products of the first amplification for a further 30 cycles, the following results were obtained as shown in FIG. 1. Lanes 2-5 and 7-8 all contain DNA from the sample obtained from subject #1366571. A presumptively strongly positive band for the ALSV LTR of expected size of 213 bp was obtained with the LTR primers designated AL1D (SEQ ID NO: 1)/L2B (SEQ ID NO: 2) (Lane 2). The positivity of this band was confirmed separately by a set of nested primers nprA181 (SEQ ID NO: 3)/nprA308 (SEQ ID NO: 4) and a set of semi-nested primers nprA27 1 (SEQ ID NO: 5)/AL2B (SEQ ID NO: 2), which gave bands of the expected sizes of 128 bp and 100 bp, respectively (Lanes 7 & 8). The strong band of around 150 hp above the expected 1 28 bp in Lane 7 is most likely DNA amplified by excess AL1D (SEQ ID NO: 1) primer from the first amplification and nprA308 (SEQ ID NO: 4). The other LTR primers RAVO-1 (SEQ ID NO: 6) & 2 also gave a positive band of the expected 99 bp size, (Lane 4). Similarly, the control Kras primers gave a positive band of size 161 bp as expected (Lane 5), while no band was seen in Lane 6 which contained all PCR reagents, but without any DNA sample (negative control). No band was obtained with the p19 1 & 2 primer set, save for a smear (Lane 3). Identical results were obtained for the ALSV primers on repeat of this experiment (on 15 Feb. 1997) using a fresh sample of DNA, and fresh PCR reagents. No further tissue was available for testing, as the initial amount of this sample was very tiny.

PCR Results for Other Human Tumor Samples

The four other human samples were tested concomitantly in the same PCR run, using the same master mix of PCR reagents for each primer set, thus only the DNA was different in these reaction mixtures. As with sample#13366571, no band was visible after the first amplification for 30 cycles this time, for any of the samples (results not shown). The results for samples #0731793, #1765805, #1832107, and #9190300, after the re-amplification of PCR products of the first amplification for a further 30 cycles are given in FIGS. 2-5. As seen in FIGS. 2-4, samples #0731793, #1765805 and #1832107, gave positive bands with all the LTR primer sets AL1D (SEQ ID NO: 1)/AL2B (SEQ ID NO: 2), nprA181 (SEQ ID NO: 3)/nprA308 (SEQ ID NO: 4), and nprA271 (SEQ ID NO: 5)/AL2B (SEQ ID NO: 2) (Lanes 4, 5 & 6), respectively, thus confirming the presence of integrated ALSV LTR. As with sample #1366571, the p19 1 & 2 primer set did not give a discernible band for these samples also, only a smear was present (Lane 7). However, on re-amplifying first amplification PCR products for only I 0 cycles (i.e. a total of 40 cycles) instead of 30 cycles (a total of 60 cycles) the smear disappeared, but no band was evident (Lane 8). The negative control containing all PCR reagents but no DNA gave negative results in each instance, as expected (Lane 2). Kras primers gave a positive band as expected (Lane 3). As seen in FIG. 5, sample #9190300 gave a negative result with the primer set AL ID (SEQ ID NO: 1)/AL2B (SEQ ID NO: 2) (Lane 4), but a clearly positive result with the nested primer set nprA181 (SEQ ID NO: 3)/nprA308 (SEQ ID NO: 4) (Lane 5). The semi-nested primer set nprA271 (SEQ ID NO: 5)/AL2B (SEQ ID NO: 2) did not give a visible band of the expected size in this sample (Lane 6). Sometimes the primer sets which include the AL2B (SEQ ID NO: 2) primer do not give a visible band even though virus is present. The confirmation of a positive band in such a case is found using the truly nested primers. As with the other human samples, p 19 primers gave negative results (Lanes 7 & 8), and the Kras primers gave a positive result for this sample (Lane 3). FIGS. 6 and 7 show the results for DNA from an ALSV-induced chicken tumor, i.e. positive control (LL3B) and from normal chicken cells, i.e. negative control (C3D), respectively. Of the LTR primers, only the nested primer set nprA181 (SEQ ID NO: 3)/nprA308 (SEQ ID NO: 4) gave a positive result for samples LL3B & C3D (Lane 5, FIGS. 6 & 7). The p 19 primer set gave a smear for these samples when the number of second amplification cycles was 30 (Lane 7, FIGS. 6 & 7). However, when the number of cycles was reduced to only 10 (a total of 40, rather than 60 cycles) a positive band was obtained for sample C3D, while sample LL3B was clearly negative (Lane 8, FIGS. 6 & 7).

Tumor DNA from a total of 16 subjects who died of cancer have been tested. In addition, the DNA from peripheral blood lymphocytes from a total of 90 healthy living subjects without known cancer has also been tested. Of the six tumor samples from subjects known to have potential for occupational exposure to ALSV, five were positive on repeated occasions. Of 10 tumor samples from subjects not known to be occupationally exposed to ALSV, only one sample was confirmed positive. However, this subject was known to have worked in a slaughterhouse where cattle, pigs, and sheep were killed, but data were not available as to whether he also worked in a poultry slaughtering house. DNA samples from 45 healthy workers occupationally exposed to ALSV, and 45 controls in the general population without occupational exposure to ALSV were consistently negative on repeated occasions. In other words, ALSV virus could not be detected in a total of 90 apparently healthy subjects, 45 of these subjects had known occupational exposure to ALSV.

Thus, the method of the present invention is useful in detecting the propensity to develop ALSV-induced cancer and infection. Once the ALSV virus integrates permanently into the host genome, the likelihood of tumor development is significantly increased. Thus, routine screening of ALSV-exposed individuals using the method of the present invention would allow early detection of ALSV integration and thus early detection of ALSV-induced cancer and infection. With repeated testing of a healthy subject, for example but not limited to an annual basis, it is possible to detect integrated virus even before the pending cancer becomes clinically evident. Early cancer detection significantly increases survival.

If this invention method is used to screen the tissue of someone with already clinically evident cancer, determining the presence or absence of ALSV integration is still useful. Knowing the causative agent is helpful in designing a treatment strategy. Detection of the integrated pro virus in an individual diagnosed with cancer would indicate the specific cause of the cancer which would then influence subsequent treatment strategy. For example, it would be important to know if the development of a lung cancer in a patient was due to cigarette smoke or to the integration of an ALSV virus. Detection of ALSV virus in that individual would then allow the possibility to develop gene therapies or antibody therapies that target specifically, that integrated virus.

Sequencing Results

Twenty microliters of the PCR product of each human tumor sample and sample LL3B Jan. 6, 1999, obtained after the second amplification with each of the ALSV LTR primers (AL ID (SEQ ID NO: I) AL2B (SEQ ID NO: 2); nprA181 (SEQ ID NO: 3)/nprA308 (SEQ ID NO: 4); nprA271 (SEQ ID NO: 5)/AL2B (SEQ ID NO: 2)), were sent to Commonwealth Biotechnologies Inc., Richmond Va., for sequencing. The results obtained are given in FIG. 8, for the templates amplified by AL1D (SEQ ID NO: 1) (forward) and AL2B (SEQ ID NO: 2) (backward primers). Using sample #R-1366571 as standard, it was compared with all LTR sequences listed in GenBank. This sample showed closest homology with subgroup A isolates #L29198 (Schmidt-Ruppin) and #VO 1168 in the GenBank, for which there was perfect homology for at least 210 of the possible 213 bases (99%). There were two discrepancies, a T instead of the C in position 3, and a G instead of the A in position 202, present in these two GenBank isolates. In position 1, the base for sample #R-366571 was unknown. Sample#1765805 showed the next closest homology to the two GenBank sequences, with disagreement in positions 1, 3, 43, & 202. Sample #0731793 showed the greatest divergence from the GenBank isolates, involving differences in six positions (36, 43, 97, 134, 174, 176), even though sequence data were not available for 63 base positions for this sample. Strains detected in humans are wild-type, and therefore are expected to be different from the GenBank strains which have been propagated in the laboratory. The positive control chicken tumor induced by ALSV (sample LL3B) showed homology at 181 of the possible 183 positions for which sequence information was available, when compared with the GenBank sequences, with disagreement at only positions 43 & 202. A plasmid ALSV DNA designated pALSV which we had handled in the laboratory on a regular basis was different from the GenBank isolates at also two positions (137 & 202). LL3B and pALSV showed almost 100% homology with human sample #R-1366571, with disagreement in each case at a single different position (43 & 137, respectively). LL3B and pALSV differed from sample #1832107 at four positions in each case, but the differences for LL3B (positions 36, 39, 43, 46) were not all the same as those for pALSV (positions 36, 39, 46, 137). Sample #1832107 also differed from sample R-1366571 in four positions (29, 36, 39, 46). In at least five positions, LL3B differed from human sample #0731793 (36, 97, 134, 174, 176), while pALSV differed from sample #0731793 in at least seven positions (36, 43, 97, 134, 137, 174, 176). Sequence analyses for the bands initially amplified by the nested or semi-nested primers (results not shown) were in perfect agreement with those for the bands amplified by the AL1D (SEQ ID NO: 1)/AL2B (SEQ ID NO: 2) primer set shown in FIG. 8. Also, in every case above, templates sequenced using the forward primer of a pair showed 100% homology with the corresponding templates sequenced by the backward primer.

Human exposure to viruses of the ALSV group is virtually universal. The highest exposure occurs among subjects involved in the slaughtering and processing of poultry. Cuts and penetrating wounds from bone splinters, knives and cutting machine blades, and frequent occurrence of dermatitis in these workers, offer a ready access for microbial agents to enter the body. Aerosol transmission of microbial agents is also well documented in abattoirs. 17 (Harris, 1962). These workers have intimate contact with internal organs and blood of poultry birds, of which as many as 175,000 can be slaughtered in a day, in a typical large slaughtering plant. Other occupational groups with potential high exposure include veterinarians, laboratory workers and other workers in the meat and food industries. Exposure of the general population is virtually universal, since the viruses are found in commercial eggs and poultry destined for human consumption, and have been shown to survive and remain fully infectious in eggs stored at 8° C. for more than 30 days. 1 The general population can also be exposed when inoculated with vaccines grown on ALSV-contaminated chicken embryo cells, or through the potential use of ALSV as vectors in gene therapy. Thus whether ALSV can infect and cause cancer in humans is of importance. The results in this study indicate the unequivocal presence of ALSV LTR integrated in the DNA extracted from cancer cells obtained from all five subjects who were members of a Baltimore cohort we had studied and who died of cancer.[3,6,8,9] Three of these workers had definite high exposure to ALSV while working in poultry slaughtering plants, and one with a possible exposure to ALSV while working in a cattle/sheep/pig abattoir/processing plant which also had an egg candling unit. No evidence was available as to whether the fifth subject had occupational exposure to ALSV. It is unlikely that the results obtained could have been due to contamination, since all the PCR reactions with all reagents present except DNA, which were run concomitantly with all the other samples, were always consistently negative. Furthermore, the sequence data showed that the LTR sequences amplified differed across not only the human samples themselves, but also from the only two other sources of exogenous ALSV in our laboratory (LL3B and pALSV). This LTR integration was confirmed using two different sets of primary LTR primers, and two sets of nested or semi-nested primers, and also by oligonucleotide sequencing. DNA extracted separately from a paraffin block of bronchial washings and a paraffin block of lung biopsy tissue from the same subject #1765805 showed identical sequences, hence it is also unlikely that the differences seen between all the samples are due to mutations induced during PCR or contamination. Also, DNA from 45 healthy poultry workers and 45 general population healthy controls which we had available was also negative using the AL1D (SEQ ID NO: 1)/AL2B (SEQ ID NO: 2) and nprA181 (SEQ ID NO: 3)/nprA308 (SEQ ID NO: 4) primers. Taken together, these observations constitute the first evidence that ALSV is involved in human carcinogenesis. In successful ALSV infection and integration in chickens, the natural host for ALSV, characteristically the LTR is always present, whereas the other genes may be absent if the virus is defective.18 (Kung & Maihle, 1987). Because of this, our strategy was to first test for presence of ALSV integration in human DNA using LTR primers. The set of p19-1 (SEQ ID NO: 8) and p19-2 (SEQ ID NO: 9) primers failed to amplify any segment of the p19 gag gene in the human and chicken tumors that were positive for ALSV LTR. This could indicate that the integrated virus is defective for at least this segment of the gag gene in these tumors, especially as the p 19 gag gene was amplified in the normal chicken tissue sample C3D, probably as part of endogenous ALSV. Both fully replication-competent and defective virus can cause cancer. Because the LTR is always present in tumors, the LTR sequences were used as primers in the present invention. Structural genes such as gag do not have to be present, thus gag sequences may or may not detect the presence of an ALSV provirus in a host genome. The virus can cause cancer in the absence of the gag gene. Thus, the gag gene sequences may not be as useful as the LTR sequences in detecting ALSV pro virus using the PCR based assay of the present invention.

It is of interest to know whether this ALSV integration occurs at specific sites in the host cellular genome, such as close to a cellular oncogene or a tumor suppressor gene, or whether other viral genes such as a viral oncogene is involved. If this is the case, additional primers directed to these genes in combination with the LTR primers may also be useful in determining whether or not ALSV has integrated into the host genome. Additionally, if a specific oncogene or tumor suppressor gene is involved, such knowledge will help in the diagnosis and treatment of patients.

This report of the presence of integrated ALSV LTR in the DNA of human subjects dying from cancer should be viewed against the following background: 1) integration is observed in tumor DNA from ALSV-exposed or potentially exposed subjects, but not in DNA from healthy ALSV-exposed human subjects and controls; 2) recent analytic epidemiologic studies have now clearly established that subjects with high occupational exposure to ALSV have excess risk of certain cancers,[3,6,8,9] thus confirming the many previous reports of indirect association between the occurrence of human cancer and putative exposure to ALSV; 1 3) while the presence of antibodies to ALSV has been clearly demonstrated in the sera of both poultry workers and members of the general population before,[14,16] the present invention demonstrates the presence of integrated ALSV provirus almost exclusively in ALSV-exposed individuals who have died of cancer; 4) experimentally, ALSV has been shown capable of infecting and transforming human cells in vitro,[19,20] 6) ALSV can infect and induce tumors in primates.[1]Taken together, this body of evidence indicates that ALSV is involved in human carcinogenesis. Thus, the method of the present invention demonstrates that ALSV detection in tissue samples from humans can be used to determine the propensity to develop, diagnose, and treat ALSV-induced cancer.

Methods

DNA Extraction

Sections of a block of embedded tumor tissue 5 micron thick were cut with a microtome, using a fresh blade for each block. Using a fresh toothpick for each block, 10 to 15 slices of tissue were picked up and deposited in a sterile 1.5 ml Eppendorf tube. The microtome blade holder and surrounding area and receiving dish were cleaned with ethanol between blocks. DNA was extracted from paraffin sections using a modified version of the method previously described by Navone et al.[21] Paraffin was removed from the dissected tissue with 1 ml of xylene, vortexed briefly, incubated at 37° C. for 15 minutes, and then centrifuged at 14,000 revolutions per minute (rpm) for 10 minutes. Xylene was decanted, leaving the tissue sediment at the bottom of the tube. Fresh xylene was added to the tissue and the process repeated. After the second xylene decantation, 1 ml of 100 percent ethanol was added to the tube, the contents briefly vortexed, incubated at room temperature for 5 minutes, and then centrifuged at 14,000 rpm for 10 minutes. Ethanol was decanted, and fresh ethanol added to the precipitate, and the process repeated. After the second ethanol decantation, the precipitate was air-dried at room temperature for 30 minutes, and re-suspended in 200 ul (microliters) of sterile water or TE (Tris/EDTA). The contents were boiled for 5 to 8 minutes to lyse the cells and release the DNA, and then centrifuged at 14,000 rpm for 5 minutes, after which 20 ul of the supernatant was used directly in a PCR reaction without further cleaning or extraction.

Detection of Integrated Virus by Polymerase Chain Reaction (PCR)

A set of oligonucleotide primers designated AL1 D (SEQ ID NO: 1) (sense) with sequence of 5'-ATCGTGCCTTATT-AGGAA, identified as SEQ ID NO: 1, and AL2B (SEQ ID NO: 2)(antisense) with sequence of 5'-ATGAAGCCTTC-CGCTTCAT, identified as SEQ ID NO: 2, were prepared from the long terminal repeat (LTR) segment of ALSV (See Table I for sequence names and numbers). These primers amplify a 213 base pair (bp) product and are derived from a highly conserved region of the LTR. We have previously tested this set of primers on ALSV plasmid DNA and DNA from ALSV-induced chicken tumors and it was always positive in these samples, and negative in DNA samples from healthy human subjects.

TABLE 1

Sequence names and numbers

| Name | SEQ ID NO | Sequence 5'-3' | Base Pairs |
|---|---|---|---|
| AL1D | SEQ ID NO: 1 | ATCGTGCCTTATTAGGAA | 18 |
| AL2B | SEQ ID NO: 2 | ATGAAGCCTTCCGCTTCAT | 19 |
| nprA181 | SEQ ID NO: 3 | CAGACGGGTCTAACATGGATTGGA | 24 |
| nprA308 | SEQ ID NO: 4 | ACCCAGGTGCACACCAATGTGG | 77 |
| nprA271 | SEQ ID NO: 5 | GCCATTTTACCATTCACCAC | 20 |
| RAVO-1 | SEQ ID NO: 6 | CCATTTTACCATTCACCACATT GGT | 25 |

TABLE 1-continued

| Sequence names and numbers | | | |
|---|---|---|---|
| Name | SEQ ID NO | Sequence 5'-3' | Base Pairs |
| RAVO-2 | SEQ ID NO: 7 | ATGAAGCCTTCTGCTTCATTCA GGT | 25 |
| p19-1 | SEQ ID NO: 8 | ATCGGGAGAGTTAAAAACCTGG GGA | 25 |
| p19-2 | SEQ ID NO: 9 | CGGACCTGGGGGAGAGACCCTC CCT | 25 |
| Kras-A | SEQ ID NO: 10 | ATTTTTATTATAAGGCCTGCTG AAA | 25 |
| Kras-B | SEQ ID NO: 11 | ATATGCATATTAAAACAAGATT TAC | 25 |
| S-Au | SEQ ID NO: 12 | CCACATTGGTGTGCACCTGGGT | 77 |
| A-Au | SEQ ID NO: 13 | AGCCTTCCGCTTCAT | 15 |
| Sn271J | SEQ ID NO: 14 | GCCATTTTACCTCCCACCAC | 20 |
| A-AuJ | SEQ ID NO: 15 | AGCCATCCGCTTCAT | 15 |
| SS-Au | SEQ ID NO: 16 | CACCACATTGGTGTGC | 16 |
| AA-Au | SEQ ID NO: 17 | ATGAAGCCTTCCGCTTCAT | 19 |
| NAL2B | SEQ ID NO: 18 | ATGAAGCCTTCTGCTTCAT | 19 |
| ALXB | SEQ ID NO: 19 | AGCCTTCTGCTTCATGCA | 18 |
| ALIVF1 | SEQ ID NO: 20 | GGATTGGACGAACCACTGAATT | 72 |
| ALIVR1 | SEQ ID NO: 21 | AGGGAATCAACGGTCCGGCC | 20 |
| J1F | SEQ ID NO: 22 | GTAACGATAAAACAGCAA | 18 |
| J2F | SEQ ID NO: 23 | TGTATTTAAGTGCCTAGC | 18 |
| J1R | SEQ ID NO: 24 | GTCAGGGAATCGACGGTCCGGC CATCA | 27 |
| J2R | SEQ ID NO: 25 | CGGTCCGGCCATCAACCCA | 19 |
| J3R | SEQ ID NO: 26 | GGTAAAATGGCGTTTATTGT | 20 |

We also employed nested primers to confirm any presumptively positive bands obtained with AL1D (SEQ ID NO: 1)/AL2B (SEQ ID NO: 2) primers. Two separate sets of primers nested within the AL1D/AL2B segment were designed, 1) nprA181 (SEQ ID NO: 3) (5'-CAGACGGGTCTAACATGGATTGGA) and nprA308 (SEQ ID NO: 4) (5'-ACCCAGGTGCACACCAATGTGG) which amplify a 128 bp segment 2) nprA271 (SEQ ID NO: 5) (5'-GCCATTTTACCA TTCACCAC and AL2B (SEQ ID NO: 2) which amplify a 100 bp segment.

We also used two other sets of primers—1) RAVO-1 (SEQ ID NO: 6) (5' CCATTTACCATTCACCACATTGGT). SEQ ID NO: 6 and RAVO-2 (SEQ ID NO: 7) (5' ATGAAGCCTTCTGCTTCATTCAGGT), SEQ ID NO: 7 which amplify a 99 bp segment of the ALSV LTR, and 2) p19-1 (SEQ ID NO: 8) (5' ATCGGGAGAGTT AAAAACCTGGGGA), SEQ ID NO: 8 and p19-2 (SEQ ID NO: 9) (5' CGGACCTGGGGGAGAGACCCTCCCT), SEQ ID NO:9 which amplify a 130 bpsegmentofthep19 ALSV gag gene. Both of these sets of primers consistently gave positive results in PCR assay when used on chicken genome known to contain integrated ALSV. The set of control primers used to monitor the integrity of the human DNA samples was Kras-A (SEQ ID NO: 10) (5'-ATTTTTATTATAAGGCCTGCTGAAA), SEQ ID NO: 10 and Kras-B (SEQ ID NO: 11) (5'-ATATGCATATTAAAACAAGATTTAC), SEQ ID NO: 11 which amplify a 161 bp segment. An additional primer set that we used included Sn271J NO: 14) and A-AuJ SEQ ID NO: 15.

For PCR, two separate reactions were run on a Perkin-Elmer DNA Thermal Cycler Model 480, using PCR reagents from Applied Biosystems—The first 100 uL reaction contained 20 uL of the supernatant containing sample DNA, 16 ul of dNTP mix (final concentration of 200 uM of each dNTP), 10 uL of Gene Amp 10× buffer (100 mM Tris-HCL pH 8.3 at 25° C.; 500 mMKCl; 15 mM MgC12; 0.01% w/v gelatin) 0.5 uL (2.5 units) of Perkin Elmer AmpliTaq DNA polymerase, 5 uL each (1 uM) of primers AL1D (SEQ ID NO: 1) and AL2B (SEQ ID NO: 2), and 43.5 uL of sterile water. Reaction conditions consist of denaturing at 94° C. for 1 minute, annealing at 37° C. for 1 minute, and extending at 72° C. for 2 minutes, and amplifying for 35 cycles. In the second 100 uL reaction, 20 uL of PCR product from the first reaction is reamplified using fresh reagents under the same conditions as the first reaction, except that the annealing temperature is increased to 50° C., Taq is increased from 0.5 uL to I uL, volume of water is 43 ul and the number of cycles is now 30. Primers used in this second reaction include AL1D (SEQ ID NO: 1) and AL2B (SEQ ID NO: 2), control primers, and the nested and seminested primers, at the same concentrations.

Electrophoresis of 8 ul each of PCR product combined with 2 ul bromophenol blue dye, was conducted on 2% Nusieve 3:1 agarose gel (FMC Bioproducts, Richland, Me.) at 70 volts for one and a half hours, using the BRL Model 400 power unit from Life Technologies. Both the gel and electrophoresis bath fluid contained ethidium bromide at a concentration of 50 ug/100 ml.

Sequencing of Amplified PCR Product

Direct sequencing of PCR products was performed by Commonwealth Biotechnologies Inc. Richmond, Va. using the ABI Dye Terminator Cycle Sequencing Ready Reaction Kit, with AmpliTaq DNA Polymerase, FS by Perkin Elmer Corporation, Foster City, Calif. The AmpliTaq DNA Polymerase, FS was developed specifically for fluorescent cycle sequencing with both dye-labeled primers and terminators. Sequence analysis was performed on the ABI 373A DNA Sequencer by Perkin Elmer Corporation.

LTR primers will always detect virus if present as these sequences are needed to integrate into the host genome. Other primers such as those based on the sequences of the gag or env genes will not always do so. Therefore, an LTR-based assay is the most sensitive. The LTR s primers used in the assays described herein were designed to be from the most highly conserved areas of the LTR, therefore they are quite sensitive to a variety of different ALSV strains. Other LTR primers may work as well, either singly or in combination with the ones described herein. However, they may be less able to detect as many different strains of ALSV as the ones described in this application either singly or in combination.

We have gone further to develop LTR primers that can be used in this assay to distinguish between exogenous and endogenous ALSV infection or genomic integration in any biological sample, including that of chicken origin. One such primer set is S-Au (SEQ ID NO: 12): 5' CCACATTG-GTGTGCACCTGGGT, SEQ ID NO: 12 and A-Au (SEQ ID NO: 13): 5' AGCCTTCCGCTTCAT, SEQ ID NO: 13 (primer concentrations in excess of 1 uM may be necessary in first-round amplification reactions, when the primer A-Au (SEQ ID NO: 13) is involved). Results obtained with the set of primers S-Au (SEQ ID NO: 12)/A-Au (SEQ ID NO: 13) or AL1D (SEQ ID NO: 1)/A-Au (SEQ ID NO: 13), in combination with results obtained using the various primer sets above such as RAVO 1 & 2, etc. can be used to clearly distinguish exogenous from endogenous ALSV infection. This additional feature makes this assay potentially the most sensitive and specific test ever for the detection of ALSV infection in all biological samples of animal origin. The invention applies to any cell or tissue of humans and animals, fresh or embedded.

References

1. Johnson, E. S. Cancer Detect. Prev. 18, 9-30 (1994).
2. Johnson, E. S., Fischman, H. R., Matanoski, G. M., Diamond, E. *J Occup. Med.* 28, 23-32 (1986).
3. Johnson, E. S., Fischman, H. R., Matanoski, G. M., Diamond, E. Br. *J Ind. Med.* 43, 597-604 (1986).
4. Johnson, E. S. *J Occup. Med.* 31, 270-272 (1989).
5. Johnson, E. S. *J Natl. Cancer Inst.* 83, 1337-1339 (1991).
6. Johnson, E. S. *Occup. Environ. Med.* 51, 541-547 (1994).
7. Johnson, E. S., Dalmas, D., Noss, J., Matanoski, G. M. *Am. J. Ind. Med.* 27, 389-403 (1995).
8. Johnson, E. S., Shorter, C., Rider, B., Jiles, R. *Int. J Epidemiol.* 26, 1142-1150 (1997).
9. Metayer, C., Johnson, E. S., Rice, J. *Am. J Epidemiol.* April 1998-147, 727-738 (1998).
10. Coggon, D., Pannett, B., Pippard, E. C., Winter, P. D. *Brit. J Ind. Med.* 46, 188-191 (1989).
11. Reif, J. S., Pearce, N. E., Fraser, J. *Scand. J. Work Environ. Health* 15, 24-29 (1989).
12. Siemiatycki, J. Ed. *CRC Press. Boca Raton, Ann Arbor, Boston, London.* 1991. pp 225-226.
13. Guberan, E., Usel, M., Raymond, L., Fioretta, G. *Br. J Ind. Med.* 50, 1008-1016 (1993).
14. Johnson, E. S., Nicholson, L. G., Durack, D. T. *Cancer Det. Prev.* 19, 394-404 (1995).
15. Johnson. E. S., Overby, L., Philpot, R. *Cancer Det. Prev.* 19, 472-486 (1995).
16. Choudat, D., Dambrine, G., Delemotte, B., Coudert, F. *Occup. Environ. Med.* 53, 403-410 (1996).
17. Harris, M. M., Hendricks, S. L., Gorman, G. W., Held, J. R. *Public Health Rep.* 77, 603-604 (1962).
18. Kung, H.-J., Maihle, N. J. Molecular basis of oncogenesis by non-acute avian retroviruscs. In: Avian Leukosis. Ed. G. F. De Boer. Martinus Nijhoff Publishing, pp 77-99, 1987.
19. Jensen, F. C., Girardi, A. J., Gilden, R. V., et al. *Proc. Natl. Acad. Sci.* (USA) 52, 53-59 (1964).
20. Stenkvist, B., Ponten, J. *Acta Pathol. Microbiol. Scand* 62, 315-330 (1964)
21. Navone, N. M., Troncoso, P., Pisters, L. L., Goodrow, T. L., Palmer, J. L., Nichols, W. N., von Eschenbach, A. C., Conti, C. J. *J Natl. Cancer Inst.* 85, 1657-1669 (1993).

TABLE II

First Amplification SUBGROUP J SAMPLES (Part 1 - Left Side)

OUR NEWLY OR PREVIOUSLY DEVELOPED PRIMERS

| Primers | ALID NAL2B 205 bp | ALID ALIVR1 167 bp | ALIVF1 NAL2B 171 bp | RAVO-1 RAVO-2 99 bp | nprA181 nprA308 128 bp | J1F JIR 265 bp | J1F J2R 252 bp | J2F JIR 97 bp |
|---|---|---|---|---|---|---|---|---|
| 0.001 μg DNA | | 8 | | 7 | 9 | 1 | 1 | 8 |
| N = 9 | | (89%) | | (78%) | (100%) | (11%) | (11%) | (89%) |
| 0.005 μg DNA | 0 | 8 | 0 | 9 | 9 | 3 | 2 | 9 |
| N = 9 samples | (0%) | (89%) | (0%) | (100%) | (100%) | (33%) | (22%) | (100%) |
| 0.05 μg DNA | 0 | 19 | 0 | 21 | 21 | 7 | 3 | 20 |
| N = 21 samples | (0%) | (90%) | (0%) | (100%) | (100%) | (33%) | (14%) | (95%) |
| 0.5 μg DNA | 0 | 9 | 0 | 20 | 12 | 3 | 0 | 3 |
| N = 21 samples | (0%) | (43%) | (0%) | (95%) | (57%) | (14%) | (0%) | (14%) |

First Amplification SUBGROUP J SAMPLES (Part 2 - Right Side)

PUBLISHED PRIMERS

| H5/ADI 295-326 bp | H5 H7 545 bp | H5 H2 764 bp | 6F 2R 2.4 kbp | HPRS-103F1 HPRS-103R 436 bp | HPRS-103F2 HPRS-103R 436 bp | Control |
|---|---|---|---|---|---|---|
| 5 | 0 | 0 | 0 | 0 | 1 | 5 |
| (56%) | (0%) | (0%) | (0%) | (0%) | (11%) | (56%) |
| 6 | 2 | 0 | 0 | 0 | 3 | 0 |
| (67%) | (22%) | (0%) | (0%) | (0%) | (33%) | (0%) |
| 14 | 4 | 0 | 0 | 2 | 2 | 0 |
| (67%) | (19%) | (0%) | (0%) | (10%) | (10%) | (0%) |
| 9 | 1 | 0 | 0 | 0 | 0 | 0 |
| (43%) | (5%) | (0%) | (0%) | (0%) | (0%) | (0%) |

*The same 9 samples were tested with both 0.001 μg DNA and 0.005 μg DNA

TABLE III

Second Amplification SUBGROUP J SAMPLES (Part 1 - Left Side)

OUR NEWLY OR PREVIOUSLY DEVELOPED PRIMERS

| | | | | | | | | | | | | |
|---|---|---|---|---|---|---|---|---|---|---|---|---|
| $1^{st}$ Round Primer Pairs | ALID NAL2B 205 bp | ALID NAL2B 205 bp | ALID NAL2B 205 bp | ALID ALIVR1 167 bp | ALIVF1 NAL2B 171 bp | J1F JIR 265 bp | J1F JIR 265 bp | J1F JIR 265 bp | J1F J2R 252 bp | J2F J1R 97 bp | nprA181 nprA308 128 bp | RAVO-1 RAVO-2 99 bp |
| $2^{nd}$ Round Primer Pairs | ALID ALIVR1 167 bp | ALIVF1 NAL2B 171 bp | ALIVF1 ALIVR1 133 bp | ALIVF1 ALIVR1 133 bp | ALIVF1 ALIVR1 133 bp | J1F J3R 211 bp | J2F J1R 97 bp | J2F J2R 84 bp | J2F J2R 84 bp | J2F J2R 84 bp | nprA181 nprA308 128 bp | RAVO-1 RAVO-2 99 bp |
| 0.001 μg DNA N = 9 | 8 (89%) | 0 (0%) | 0 (0%) | 3 (33%) | 0 (0%) | 6 (67%) | 2 (22%) | 1 (11%) | 7 (78%) | 1 (11%) | 9 (100%) | 8 (89%) |
| 0.005 μg DNA N = 9 | 7 (78%) | 0 (0%) | 2 (22%) | 4 (44%) | 1 (11%) | 7 (78%) | 4 (44%) | 2 (22%) | 8 (89%) | 0 (0%) | 9 (100%) | 9 (100%) |
| 0.05 μg DNA N = 21 | 14 (67%) | 0 (0%) | 2 (10%) | 12 (57%) | 3 (14%) | 18 (86%) | 10 (48%) | 5 (24%) | 15 (71%) | 4 (19%) | 21 (100%) | 21 (100%) |
| 0.5 μg DNA N = 21 | 15 (71%) | 0 (0%) | 0 (0%) | 15 (71%) | 0 (0%) | 12 (57%) | 19 (90%) | 2 (10%) | 19 (90%) | 2 (10%) | 20 (95%) | 21 (100%) |

Second Amplification SUBGROUP J SAMPLES (Part 2 - Right Side)

PUBLISHED PRIMERS

| | | | | | |
|---|---|---|---|---|---|
| H5/ADI 295-326 | H5/H7 545 bp | H5/H2 764 bp | 6F/2R 2.4 kbp | HPRS-103F1 HPRS-103R 436 bp | HPRS-J03F2 HPRS-103R 436 bp |
| H5/ADI 295-326 | H5/H7 545 bp | H5/H2 764 bp | 6F/2R 2.4 kbp | HPRS-103F1 HPRS-103R 436 bp | HPRS-103F2 HPRS-103R 436 bp |
| 5 (56%) | 0 (0%) | 0 (0%) | 0 (0%) | 1 (11%) | 1 (11%) |
| 5 (56%) | 2 (22%) | 0 (0%) | 0 (0%) | 0 (0%) | 3 (33%) |
| 12 (57%) | 4 (19%) | 0 (0%) | 0 (0%) | 4 (19%) | 4 (19%) |
| 10 (48%) | 1 (5%) | 0 (0%) | 0 (0%) | 0 (0%) | 1 (5%) |

TABLE IV

First Amplification SUBGROUP A SAMPLES (22-70) (Part 1 - Left Side)

| Sample # | 1 | 2 | 3 | 4 | 5 | 6 | 7 |
|---|---|---|---|---|---|---|---|
| Sample 0.5 μg (500 ng) DNA | Primers | ALID NAL2B 205 bp | ALID ALIVR1 167 bp | ALIVF1 NAL2B 171 bp | ALIVF1 ALIVR1 133 bp | ALID ALXB 201 bp | H5 ADI 295-326 bp |
| | | 1 | 2 | 3 | 4 | 5 | 6 |
| Samples 22-37 N = 16 | | 0 (0)%) | 1 (6%) | 0 (0)%) | 8 (50%) | 0 (0)%) | 0 (0)%) |
| Samples 38-70 N = 33 | | 0 (0%) | 8 (24%) | 0 (0%) | 8 (24%) | 10 (30%) | 16 (48%) |

First Amplification SUBGROUP A SAMPLES (22-70) (Part 2 - Right Side)

| 8 | 9 | 10 | 11 | 12 | 13 | 14 |
|---|---|---|---|---|---|---|
| 1 kb Ladder | SS-Au AA-Au 86 bp | ALID AA-Au 205 bp | ALID A-Au 205 bp | ALIVF1 AA-Au 171 bp | RAVO-1 RAVO-2 99 bp | nprA181 nprA308 128 bp |
| | 7 | 8 | 9 | 10 | 11 | 12 |
| | 0 (0)%) | 0 (0)%) | 0 (0)%) | 0 (0)%) | 12 (75%) | 11 (69%) |
| | 0 (0%) | 0 (0%) | 0 (0%) | 0 (0%) | 30 (91%) | 31 (94%) |

TABLE V

Second Amplification SUBGROUP A SAMPLES (22-70) (Part 1 - Left Side)

| Lane | 1 | 2 | 3 | 4 | 5 | 6 | 7 | 8 | 9 | 10 |
|---|---|---|---|---|---|---|---|---|---|---|
| Sample # | 123<br>Ladder | | | | | | | | | |
| | Primers | ALID<br>NAL2B | ALID<br>ALIVR1 | ALIVF1<br>NAL2B | ALIVF1<br>ALIVR1 | ALID<br>ALXB | ALID<br>NAL2B | ALID<br>ALXB | ALID<br>AA-Au | nprA181<br>nprA308 |
| 500 ng<br>DNA | Primers | ALID<br>NAL2B | ALID<br>ALIVR1 | ALIVF1<br>NAL2B | ALIVF1<br>ALIVR1 | ALID<br>ALXB | ALIVF1<br>ALIVR1 | SS-Au<br>ALXB | SS-Au<br>ALXB | nprA181<br>nprA308 |
| | | 205 bp | 167 bp | 171 bp | 133 bp | 201 bp | 133 bp | 82 bp | 82 bp | 128 bp |
| | | 13 | 14 | 15 | 16 | 17 | 18 | 19 | 20 | 12 |
| Samples<br>22-37<br>N = 16 | | 0<br>(0%) | 15<br>(94%) | 0<br>(0%) | 14<br>(88%) | 13<br>(81%) | 2<br>(13%) | 14<br>(88%) | 11<br>(69%) | 16<br>(100%) |
| Samples<br>38-70<br>N = 33 | | 0<br>(0%) | 28<br>(85%) | 0<br>(0%) | 26<br>(79%) | 31<br>(94%) | 8<br>(24%) | 33<br>(100%) | 27<br>(82%) | 32<br>(97%) |

Second Amplification SUBGROUP A SAMPLES (22-70) (Part 2 - Right Side)

| 11 | 12 | 13 | 14 | 15 | 16 | 17 | 18 | 19 | 20 |
|---|---|---|---|---|---|---|---|---|---|
| | | | | | 1 Kb<br>Ladder | | | | |
| ALID<br>NAL2B | H5<br>ADI | ALID<br>AA-Au | ALID<br>NAL2B | SS-Au<br>AA-Au | | ALIVF1<br>ALIVRI | ALIVF1<br>AA-Au | ALID<br>A-Au | RAVO-1<br>RAVO-2 |
| nprA181<br>nprA308 | H5<br>ADI | SS-Au<br>AA-Au | SS-Au<br>AA-Au | SS-Au<br>AA-Au | | SS-Au<br>AA-Au | ALIVF1<br>AA-Au | ALID<br>A-AU | RAVO-1<br>RAVO-2 |
| 128 bp | 295-326 bp | 86 bp | 86 bp | 86 bp | | 86 bp | 171 bp | 205 bp | 99 bp |
| 21 | 22 | 23 | 24 | 25 | | 26 | 27 | 28 | 11 |
| 12<br>(75%) | 1<br>(6%) | 0<br>(0)%) | 0<br>(0)%) | 0<br>(0)%) | | 2<br>(13%) | 0<br>(0)%) | 0<br>(0)%) | 16<br>(100%) |
| 20<br>(61%) | 21<br>(64%) | 0<br>(0%) | 0<br>(0%) | 13<br>(39%) | | 1<br>(3%) | 1<br>(3%) | 24<br>(73%) | 33<br>(100%) |

TABLE VI

First Amplification

HUMANS SAMPLES FROM POULTRY WORKERS (Part 1 - Left Side)

| Primers | ALID<br>NAL2B<br>205 bp | ALID<br>ALIVR1<br>167 bp | ALIVF1<br>NAL2B<br>171 bp | RAVO-1<br>RAVO-2<br>99 bp | nprA181<br>nprA308<br>128 bp | J1F<br>JIR<br>265 bp | J1F<br>J2R<br>252 bp | J2F<br>J1R<br>97 bp |
|---|---|---|---|---|---|---|---|---|
| 5 ng DNA<br>Total<br>N = 10<br>Samples from<br>4 Subjects in<br>Arkansas | —<br>(0%) | 7<br>(70%) | —<br>(0%) | 6<br>(60%) | 10<br>(100%) | —<br>(0%) | —<br>(0%) | 9<br>(90%) |
| 5 ng DNA<br>Total<br>N = 4 Samples<br>from 4<br>Subjects in<br>Maryland | —<br>(0%) | 4<br>(100%) | —<br>(0%) | —<br>(0%) | 4<br>(100%) | —<br>(0%) | —<br>(0%) | 4<br>(100%) |

HUMANS SAMPLES FROM POULTRY WORKERS (Part 2 - Right Side)

| 1 kb Ladder | H5/ADI<br>295-326 bp | H5<br>H7<br>545 bp | H5<br>H2<br>764 bp | 6F<br>2R<br>2.4 kbp | HPRS-103F1<br>HPRS-103R<br>436 bp | HPRS-103F2<br>HPRS-103R<br>436 bp | Control |
|---|---|---|---|---|---|---|---|
| | 2<br>(20%) | —<br>(0%) | | | —<br>(0%) | —<br>(0%) | —<br>(0%) |
| | 1<br>(25%) | —<br>(0%) | | | —<br>(0%) | —<br>(0%) | —<br>(0%) |

TABLE VII

Second Amplification

HUMANS SAMPLES FROM POULTRY WORKERS (Part 1 - Left Side)

| | | | | | | | | | |
|---|---|---|---|---|---|---|---|---|---|
| 1st Round Primers 5 ng DNA | ALID NAL2B 205 bp | ALID NAL2B 205 bp | ALID NAL2B 205 bp | ALID ALIVR1 167 bp | ALIVF1 NAL2B 171 bp | J1F JIR 265 bp | J1F JIR 265 bp | J1F JIR 265 bp | J1F J2R 252 bp |
| 2md Round Primers 10 ul PCR product | ALID ALIVR1 167 bp | ALIVF1 NAL2B 171 bp | ALIVF1 ALIVR1 133 bp | ALIVF1 ALIVR1 133 bp | ALIVF1 ALIVR1 133 bp | J1F J3R 211 bp | J2F J1R 97 bp | J2F J2R 84 bp | J2F J2R 84 bp |
| Total N = 9 Samples from Arkansas | 5 (56%) | — (0%) | 2 (22%) | 8 (89%) | 4 (44%) | — (0%) | 5 (56%) | 5 (56%) | 3 (33%) |
| Total N = 4 Samples from 4 Subjects in Maryland | 4 (100%) | — (0%) | — (0%) | 4 (100%) | — (0%) | — (0%) | 1 (25%) | 3 (75%) | 4 (100%) |
| | 2 | 3 | 4 | 5 | 6 | 7 | 8 | 9 | 10 |

HUMANS SAMPLES FROM POULTRY WORKERS (Part 2 - Right Side)

| | | | | | | | | | |
|---|---|---|---|---|---|---|---|---|---|
| J2F J1R 97 bp | H5/ADI 295-326 | H5 H7 545 bp | J1F/JIR 265 bp | nprA181 nprA308 128 bp | RAVO-1 RAVO-2 99 bp | J1F/J2R 252 bp | HPRS-103F1 HPRS-103R 436 bp | HPRS-103F2 HPRS-103R 436 bp | J2F/J1R 97 bp |
| J2F J2R 84 bp | H5/ADI 295-326 | H5 H7 545 bp | J1F/ JIR 265 bp | nprA181 nprA308 128 bp | RAVO-1 RAVO-2 99 bp | J1F J2R 252 bp | HPRS-103F1 HPRS-103R 436 bp | HPRS-103F2 HPRS-103R 436 bp | J2F/ J1R 97 bp |
| 2 (22%) | 1 (11%) | 1 (11%) | — (0%)* | 9 (100%) | 7 (78%) | 2 (33%)* | — (0%) | — (0%) | 6 (100%)* |
| — (0%) | 2 (50%) | — (0%) | 4 (100%) | 4 (100%) | — (0%) | — (0%) | — (0%) | — (0%) | 4 (100%) |
| 11 | 12 | 13 | 14 | 15 | 16 | 17 | 18 | 19 | 20 |

TABLE VIII

Comparison of USDA Patent for Subgroup J with My Protocol on Subgroup Samples 1-21 (Part 1 - Left Side)

| Sample # From 2 Gels | 1 | 2 | 3 | 4 | 5 | 6 | 7 | 8 | 9 | 10 |
|---|---|---|---|---|---|---|---|---|---|---|
| Primer SEQID 3 and 4 My Protocol | – | – | – | – | – | – | – | – | – | – |
| Primer SEQID 3 and 4 USDA Patent | – | – | – | – | – | – | – | – | – | – |
| Primer B USDA Patent | – | + | + | + | + | – | + | + | – | + |
| Primer C USDA Patent | + | + | + | + | + | + | + | + | + | + |

Comparison of USDA Patent for Subgroup J with My Protocol on Subgroup Samples 1-21 (Part 2 - Right Side)

| 11 | 12 | 13 | 14 | 15 | 16 | 17 | 18 | 19 | 20 | 21 | % Detected |
|---|---|---|---|---|---|---|---|---|---|---|---|
| – | – | – | – | – | – | – | – | – | – | – | 0 (0%) |
| – | – | – | – | – | – | – | – | – | – | – | 0 (0%) |
| + | + | + | + | – | + | + | + | – | – | – | 14 (67%) |
| + | + | + | – | + | + | + | + | + | + | + | 20 (95%) |

The present invention is a method of testing a subject for a propensity to develop, diagnose, or treat ALSV-induced infection or cancer, comprising the steps of obtaining a cell, tissue, or fluid sample from the subject, processing the sample to isolate DNA from the sample, and examining the DNA isolated from the sample to detect the presence of the ALSV LTR. The sample can be from a cell, a tissue or a tumor. Preferably, the DNA is examined using a PCR-based assay with at least one primer set or any combination of the individual primers in first round or second round reactions from the group consisting of: AL1D (SEQ ID NO: 1)/AL2B (SEQ ID NO: 2), nprA181 (SEQ ID NO: 3)/nprA308 (SEQ ID NO: 4), nprA271 (SEQ ID NO: 5)/AL2B (SEQ ID NO: 2), RAVO-1 (SEQ ID NO: 6)/RAVO-2 (SEQ ID NO: 7), AL1D (SEQ ID NO: 1)/A-Au (SEQ ID NO: 13), S-Au (SEQ ID NO: 12)/A-Au (SEQ ID NO: 13), and nprA271 (SEQ ID NO: 5)/A-Au (SEQ ID NO: 13), Sn271J (SEQ ID NO: 14)/A-AuJ (SEQ ID NO: 15). The following primers are additionally added to be used in the assay in any combination, as they expand the capacity of the assay to detect specifically ALSV subtypes of the subgroup J group in addition to the other subgroups, and also defective ALSV: J1F (SEQ ID NO: 22)/J1R (SEQ ID NO: 24), J1F (SEQ ID NO: 22)/J2R (SEQ ID NO: 25), J2F (SEQ ID NO: 23)/J1R (SEQ ID NO: 24), J2F (SEQ ID NO: 23)/J2R (SEQ ID NO:

25), J1F (SEQ ID NO: 22)/J3R (SEQ ID NO: 26), AL1D (SEQ ID NO: 1)/ALIVR1 (SEQ ID NO: 21), ALIVF1 (SEQ ID NO: 20)/ALIVR1 (SEQ ID NO: 21), AL1D (SEQ ID NO: 1)/NAL2B (SEQ ID NO: 18), ALIVF1 (SEQ ID NO: 20)/NAL2B (SEQ ID NO: 18), AL1D (SEQ ID NO: 1)/ALXB (SEQ ID NO: 19). The sequences of the primers are shown in Table I.

We have developed new primers and new reaction conditions. The following new primers were developed specifically to detect ALSV subgroup J infection, which was first detected in chickens in the US in 1989, and since has presented as a major problem of ALSV infection in meat-type chickens: J1F (SEQ ID NO: 22), J2F (SEQ ID NO: 23), J1R (SEQ ID NO: 24), J2R (SEQ ID NO: 25), J3R (SEQ ID NO: 26); the following primers were developed to amplify ALSV subgroups A-D specifically: ALIVF1 (SEQ ID NO: 20), ALIVR1 (SEQ ID NO: 21); the following primer was developed to amplify ALSV subgroups A-E: NAL2B (SEQ ID NO: 18) when used in combination with our previous primer AL1D (SEQ ID NO: 1); and the following primer ALXB (SEQ ID NO: 19) was developed specifically to amplify defective avian leukemia and sarcoma viruses when used with AL1D (SEQ ID NO: 1).

We compared the performance of these new primers and two of our previous primers in U.S. Pat. No. 6,391,555,viz: nprA181/nprA308 and RAVO-1 (SEQ ID NO: 6)/RAVO-2 (SEQ ID NO: 7) with published primers for detecting different subgroups of ALSV developed by other investigators, under rigorous conditions (DNA extracted from paraffin-embedded tissues that is frequently found to be degraded). The five published primer pairs specifically developed by others to detect ALSV subgroup J are as follows: 6F/2R (which amplifies a 2,400 bp fragment) by Silva et al, 2000; HPRS-103F1/HPRS103-R and HPRS-103F2/HPRS-103R (that each amplifies a 436 bp fragment) by Smith E J et al 1998; H5/H2 (that amplifies a 764 bp fragment, and H5/H7 (that amplifies a 545 bp fragment) by Smith L M et al, 1998. A primer pair H5/ADI was developed by Smith L M et al 1998 specifically for detecting ALSV subgroups A-E.

Subgroup J Infections in Animals

As shown in Tables II-III and FIGS. 1-2, all of these primers (ours and others) were tested against DNA extracted from 21 paraffin embedded samples of experimentally induced tumors or tumors from naturally infected chickens in the field, all of which were known and confirmed to be infected with subgroup J ALSV. The results are given in Table II using different concentrations of DNA (1 ng, 5 ng, 50 ng and 500 ng) in first-round PCR reactions according to our new protocol described below. Table III gives results for second-round PCR reactions. The results in both tables show clear superiority of both our previous primers (RAVO-1 (SEQ ID NO: 6)/RAVO-2 (SEQ ID NO: 7) and nprA181 (SEQ ID NO: 3)/nprA308 (SEQ ID NO: 4)) and our new primers J1F (SEQ ID NO: 22), J2F (SEQ ID NO: 23), J1R (SEQ ID NO: 24), J2R (SEQ ID NO: 25), J3R (SEQ ID NO: 26) over published primers by others. Irrespective of the amount of DNA used in PCR reactions all the published primers specifically designed to amplify subgroup J ALSV performed very poorly detecting only 0% to 33% of the known subgroup J infections. Interestingly, the published primer pair designed to specifically amplify subgroups A-E detected up to 67% of subgroup J infections. In stark contrast our primers could detect up to 100% of subgroup J infections.

As shown in FIGS. 5-7, sequences amplified by our primers in Chicken DNA were compared against published sequences via BLAST analysis.

FIG. 5 shows a BLAST result for a segment of ALSV amplified by primer set nprA181/nprA308 in DNA extracted from chicken tissue known to be infected with subgroup J virus. The expected result is a 128 base pair fragment. The results from the 126 base pair sequence segment with both primers completely present show a 123 of 125 (98%) match indicating that the sample is positive for ALSV Subgroup J DNA (BLAST Result: Avian leukosis virus isolate 98-9 LTR, partial sequence Sequence ID: gb|AY689486.1|Length: 215).

FIG. 6 shows a BLAST result for a segment of ALSV amplified by primer set AL1D/ALIVR1 in DNA extracted from chicken tissue known to be infected with subgroup J virus. The expected result is a 172 base pair fragment. The results of the BLAST analysis of the 173 base pair sequence segment show that ALIVR1 has 1 mismatch and AL1D is completely present. The query covers 99% (172 of 173) and has an identity 98% (169 of 172) indicating that the sample is positive for ALSV Subgroup J DNA (BLAST result: Avian leukosis virus isolate UD2 envelope precursor protein (env) gene, complete cds; and 3'LTR long terminal repeat, complete sequence|Sequence ID: gb|AF307949.1|AF307949|Length: 2589).

FIG. 7 shows BLAST results for segments of ALSV amplified by primer set RAVO-1/RAVO-2 in DNA extracted from chicken tissue known to be infected with subgroup J virus. The expected result is a 99 base pair fragment. The results from the 100 base pair sequence segment with both primers completely present. The query covers 99% (99 of 100) and has identity 100% (99 of 99) indicating that the sample is positive for ALSV Subgroup J DNA (BLAST Results: *Gallus gallus* endogenous virus ALVE-B 11 genomic sequence|Sequence ID: gb|KC610517.1|Length: 7250; Avian leukosis virus strain TW-3593, complete genome|Sequence ID: gb|HM582658.1|Length: 7483).

Subgroup A infections in Animals

When tested against samples known to be positive for ASLV subgroup A infection, our primers again show clear superiority over the primer pair H5/ADI that was specifically designed to test infection with ALSV subgroups A-E. See Tables IV & V.

Although not shown, the published primers continued to perform poorly and even worse when the protocols that were described for their use were followed as closely as possible, as compared to our protocol described below.

ALSV Infections in Human Samples

As shown in Tables VI-VII and FIGS. 3-4, we also compared the performance of these same primers in DNA extracted from paraffin embedded blocks of tumor tissues from poultry workers known to have died of cancer types known to be occurring in excess from our epidemiologic studies of poultry workers. The results are given in Tables VI & VII. Ten samples from various tissues and organs of 4 poultry workers who died of cancer in Arkansas and 4 samples from 4 poultry workers who died of cancer in Maryland were tested. Our primers again show clear superiority over published primers. The best results for published primers were obtained with the primer set H5/ADI (up to 50% of infections detected). This should be compared with our primer sets that were able to detect up to 100% of infections in humans as observed also for samples originating from chickens.

The PCR results described above were confirmed by sequencing. Our primers were found to be far superior than any published thus far for detecting subgroup J infections in animal and human DNA samples extracted from paraffin embedded tissues. Because DNA in paraffin-embedded samples is frequently degraded, it is usually not suitable for amplifying long fragments of DNA. The published primers were designed to amplify fragments 436 to 2,400 bases long, while our primers were designed to amplify fragments of less than 250 bp. We believe that this difference in and the possibility our primers are derived from much more highly conserved regions of the virus than published primers and also the possibility that our protocol was more robust, are the reasons why our primers exhibit such clear superiority over published primers in detecting infections both in chickens and humans. Importantly to date our primers are the only ones reported to have the capacity to detect ALSV infection in humans.

As shown in FIG. 8, sequences amplified by our primers in Human DNA were compared against published sequences via BLAST analysis.

FIG. 8 shows a BLAST result for a segment of ALSV amplified by primer set J2F/J1R in DNA extracted from human cancer tissue from a poultry worker who died of cancer. The expected result is a 97 base pair fragment. The results from the 98 base pair sequence segment with both primers completely present. The query covers 100% (98 of 98) and identity 100%% (98 of 98) indicating that the sample is positive for ALSV Subgroup J DNA for all isolates, several of them 100% coverage and 100% identities (Avian leukosis virus isolate SD110503R, complete genome|Sequence ID: gb|KF738251.1|Length: 7708). This also includes ALSV Subgroup J from China, Russia and Newark, Del., USA.

The following is an example of a nested PCR method of a preferred embodiment of the present invention.

Methods

In first-round, reagents used in a 50 ul PCR reaction include: 1 ul of 5 ng to 50 ng of DNA, 2.5 ul containing 25 pmol of primer, 5 ul containing 200 uM of dNTP, and 0.5 ul of 2.5 units of Taq Agilent polymerase and 5 ul of 10× buffer and 33.5 ul of water. In the second-round reactions similar volumes were used except that 10 ul of PCR product was used in place of DNA and 24.5 ul of water instead of 33.5 ul.

A touchdown PCR procedure was used and the conditions were as follows:

$1^{ST}$-ROUND PCR CONDITIONS (Initial Denature 94° C./3 min);

Touch down cycle

D=94° C./1 min;

A=Step Down from 60° C. by 0.6° C.);

E=72° C. for 2 min;

No. of Cycles=40

After the 40 cycles are completed

Do Final Extension at 72° C. for 10 mins $2^{ND}$-ROUND PCR CONDITIONS (Initial Denature 94° C./1 min);

Touch down cycle

D=94° C./1 min;

A=Step Down from 60° C. by 0.6° C.);

E=72° C. for 2 min;

No. of Cycles=30

After the 30 cycles are completed

Final Extension=72° C. for 10 mins

References

Silva R F, Fadly A M, Hunt H D. Hypervariability in the envelope genes of subgroup J avian leukosis viruses obtained from different farms in the United States.

Smith E J, Fadly A M, Okazaki W. an enzyme-labeled immunosorbent assay for detecting avian leukosis-sarcoma viruses. Avian ds 1979; 23:698-707.

Smith E J, Fadly A M, Crittenden L B. Observation on an enzyme-linked immunosorbent assay for the detection of antibodies against avian leukosis-sarcoma viruses. Avian Dis 1986; 30: 488-4493.

Smith E J, Williams S M, Fadly A M. Detection of avian leukosis virus subgroup j using the polymerase chain reaction. Avian Dis 1998; 42: 375-380.

Smith L M, Brown S R, Howes K, McLeod S, Arshad S S, Barron G S, Venugopal K, McKay J C, Payne L N. Development and application of polymerase chain reaction (PCR) tests for the detection of subgroup J avian leukosis virus. Virus Res 1998; 54: 87-98.

ACKNOWLEDGEMENT

I wish to thank, Dr Richard DiAugustine and Mr Charlie Brown for their assistance and support during the initial stage of this work, and hospital pathologists in the State of Maryland who have kindly provided human paraffin tumor blocks. My thanks also Dr Stephen Hughes and Dr. Ron Swanstrom who provided me with ALSV plasmids, and Dr Richard Witter, Dr Aly Fadly and Dr Harriet Robinson who provided me paraffin blocks of chicken tumors.

The following is an example of a preferred embodiment of the present invention.

A Comparison of the Performance of a New PCR Assay and New Primers for Amplifying ALSV Subgroup J-Specific Infections and Other ALSV Subgroups with Published PCR Assays and Primers.

Introduction

The results obtained with the polymerase reaction assay depend on consideration of several parameters that include reaction conditions (temperature and duration of denaturing, anneal and extension, number of cycles of amplification), and amount or concentration of various reagents employed (dNTP, Taq enzyme, primers, buffer, magnesium, and DNA). It can be argued that these represent so many variables that should be accounted for in running reactions that ideally, a single sample has to be tested for all possible combinations before it can be declared negative. This is obviously unrealistic and impractical even under the most rigorous research protocol and certainly more so in routine diagnostic use of PCR. In practice since a laboratory has to test large numbers of samples daily, a single standard protocol is highly desirable and all samples are tested using the same protocol. Chickens are naturally infected with retroviruses of the avian leucosis/sarcoma virus (ALSV) group. The ones that naturally infect chickens and other birds are classified into subgroups A, B, C, D, E, and J. Subgroup J ALSV recently emerged in 1989 as a major problem infection in meat-type chickens that is the cause of acute myeloid leukosis. The economic cost of subgroup J infection in chickens to the poultry industry is tremendous. For example, for commercial broiler breeders in the US alone, the total loss is estimated to be 1.5% per week (Silva et al, 2000).

Efforts to control ALSV infections in both egg-laying and meat-type chickens have been in existence for decades, and the main method is to diagnose the infection in chickens and then eliminate infected flocks. This strategy has met with some success worldwide but has not resulted in elimination of infection which still continues to be a major source of economic loss to the poultry industry as these viruses commonly cause not only cancer and other debilitating diseases such as anemia in birds, but also diminished productivity. One of the main reasons for the failure to eliminate infection in flocks worldwide in spite of intensive efforts that date back as far as the 1950's or earlier, is the lack of a reliable and sensitive test for the viruses that can be conducted quickly.

At present, the gold standard is virus neutralization test, but this takes a week or longer for results to be available. Here reference avian leukosis virus (ALV) or Rous sarcoma virus (RSV) is made to react with the blood sample or serum extract containing antibody to ALSV. Antibody level is measured by its reaction with RSV and the neutralization of virus is determined by reduction in the number of foci induced by RSV (Payne & Fadly, 1997). A microneutralization test using ALV as indicator can also be conducted in 96-well microtiter plates, in which neutralization of the virus is determined by an ELISA on culture fluids. Positive ELISA indicates no antibody, while negative ELISA indicates virus neutralization and presence of antibody (Fadly & Witter, 1998). PCR has been shown to be as sensitive as or more sensitive than virus neutralization test (Smith L M et al, 1998).

The most common and widely used tests commercially available are the direct and indirect ELISA that detect the protein product of the p27 gag gene or antibodies directed against it, respectively (Smith et al 1979; Smith et al, 1986). With the direct ELISA the sample is inoculated into cultures of chick embryo fibroblasts (CEF), and virus propagation is detected by testing the supernatant fluid for the presence of p27 gs antigen by ELISA. However, the ELISA has been shown not to be sensitive when virus load is low. In one study it was found that while PCR could detect infections as early as 1, 2, and 3 days post-infection, ELISA was only able to detect infections at 7 days post infection (Smith E J et al, 1998). In another study PCR more times than not showed clear superiority over ELISA and in situations when this was not so there was reason to believe that it was because virus was absent or very low (Smith Lm et al, 1998). Thus PCR assay appears to show the greatest promise for detecting ALSV infection. To our knowledge, there is no commercial PCR kit available for subgroup J, although there is a U.S. Pat. No. 6,146,641.

Here we report on a PCR assay using newly designed primers that we developed to detect ALSV infections. These include but are not limited to the following primers sets: A (ALID/ALIVR1), B (RAVO-1/RAVO-2), C (nprA181/nprA308), D (J1F/J1R), E (J1F/J2R), and F (J2F/J1R). This report is restricted to the performance of this new assay with these primers specifically for ALSV subgroup J-infected samples. We compared our primers performance with those obtained with primer sets published in the literature designed to specifically detect subgroup J infections. These are 6F/2R (2,400 bp fragment amplified) by Silva et al, 2000; HPRS-103F1/HPRS103-R; HPRS-103F2/HPRS-103R (436 bp fragment amplified by each) by Smith E J et al 1998; H5/H2 (764 bp fragment amplified) H5/H7 (545 bp fragment amplified, and H5/ADI (295-326 bp fragment amplified) by Smith L M et al, 1998. We also conducted experiments that follow the protocol for the only patented PCR assay (U.S. Pat. No. 6,146,641 November 2000) for subgroup J avian leukosis/sarcoma viruses developed by the US Department of Agriculture that is directed against the ALSV envelope gene and amplifies a 1.7 kb fragment that encompasses portions of gp85 and gp37.

PCR Assay

Isolates of avian leukosis viruses (ALSV) were obtained from 70 independent samples collected in the field from chickens or from experimental infection. The samples were cultured for virus and confirmed to be positive by ELISA for gag antigen. Of the 70 samples, 21 were positive for subgroup J virus, 16 for RAV-1 subgroup A, and 33 for RPL-40 subgroup A. This report is restricted to the findings for the 21 subgroup-positive samples.

All the primer sets were run under the same standard step-down PCR protocol that we routinely use. Samples were tested using 0.5 μg, 0.05 μg, 0.005 μg, 0.001 μg of DNA. This is because it is already known that some of the published primers did not perform well at low DNA concentrations. Moreover, for successful eradication of ALSV infection in poultry flocks, an assay that will detect very low levels of infection in birds is a mandatory requirement. Additionally, for published primers, we also carried out separate PCR reactions under conditions that are similar as closely as possible to those described in the individual protocols in the papers, and also experiments using the USDA patented assay.

Results

Single Round Amplification

It is seen in Table II that at each concentration of DNA, our primers far outperformed published primers in detecting subgroup J infections.

When 0.5 μg DNA was used in the PCR reaction, of the 6 published primer sets 4 could not detect any of the subgroup J infections; 1 primer set (H5/H7) detected only 1 of the 21 infections (5%), and another (H5/ADI) detected 9 of 21 infections (43%). In contrast at this DNA amount, three of our primer sets successfully detected 43%, 57% and 95% of infections.

When 0.05 μg, DNA was used, four of our primer sets detected 90% to 100% of infections. In contrast, the best result for published primer sets was the 67% achieved again with H5/ADI. The findings were closely similar when 0.005 μg DNA was used.

Even at the lowest amount of DNA employed (0.001 μg) 4 our primer sets gave results (78% to 100%) that were superior to those of published primer sets (0% to 56%).

We also conducted experiments in which we followed the exact protocol as closely as possible described for the published primer sets in the publications. Our primer sets outperformed the published primer sets even under their recommended protocols (results not shown).

Double Round Amplification

Here, PCR product from first-round amplifications were amplified using either the same primer pairs used in the first round or using nested or semi-nested primers.

In Table III it is seen that irrespective of the amount of DNA that was employed in the first-round reaction, for published primers, the best results were obtained for using primer set H5/ADI (only 48% to 57% of infections detected). In contrast using 0.5 μg DNA, at least 7 of our primer sets detected 57% to 100% of infections. The superiority of our primers over published primers held using other amounts of DNA in the first round reactions. Results using the assay can be available within 8 hours.

Results Using the USDA-Patented PCR Protocol for Subgroup J.

It is seen in Table VIII that all 21 subgroup J samples were negative using both the USDA-patented primers and our primers when amplification was conducted according to the USDA-patented protocol. On the other hand, our primers B & C were able to detect 67% and 95% of the subgroup J samples even when using the USDA protocol as compared to the USDA patented primers that could not detect any positive sample.

In all the experiments we conducted on DNA extracted from paraffin blocks using primers published by others, no sample tested positive when the target segment to be amplified was greater that 550 bp. This can be because there is some degradation of DNA extracted from paraffin blocks, or because these primers are not very sensitive and are not able to detect all samples carrying ALSV. This emphasizes the superiority of our primers over those published. In fact it is known that primer pairs such as 6F/6R that is supposed to amplify a 2.1 kb ALSV fragment are not capable of detecting low levels of ALV-J infections (cited in Silva al. 2000).

CONCLUSION

We developed new PCR assays and primers for the detection of infections by ALSV subgroup J and other ALSV subgroups in poultry that can be used for other animals and humans. In both first-round and second-round amplifications of samples and PCR products, our assays and primer sets showed clear superiority over published and patented PCR assays and primers. More importantly, some of our primers could detect 100% of infections, indicating that they represent the most sensitive, specific, reliable and rapid assay developed for detecting subgroup J ALSV and other ALSV subgroup infections. Importantly, our primers gave 100% positive results on samples that are archival paraffin-embedded tissues that are typically stored over many years and which have some or significant DNA degradation. Yet our assay and primers gave excellent results even under these challenging circumstances.

In human samples different tissues from the same person had different results with some primers, which means a battery of primers may be needed in some situations.

References

Fadly A M, Witter R L. Oncornaviruses: Leukosis/Sarcoma and reticuloendotheliosis. In J R Glisson, D J Jackwood, J E Pearson. W M Reed, and D E Swayne (Eds). A laboratory manual for the isolation and identification of avian pathogens $4^{th}$ edition (pp. 185-196), (1998). Kennett Square, Pa.: American Association of Avian Pathologists.

Payne L N, Fadly A M. Leukosis/Sarcoma group. In: B W Calnek, H J Barnes, C W Beard, L R McDougald, Y M Saif (Eds). Diseases of Poultry, $10^{th}$ Ed.; pp 414-466. Iowa State University Press, Ames. Iowa.

Silva R F, Fadly A M, Hunt H D. Hypervariability in the envelope genes of subgroup J avian leukosis viruses obtained from different farms in the United States.

Smith E J, Fadly A M, Okazaki W. an enzyme-labeled immunosorbent assay for detecting avian leukosis-sarcoma viruses. Avian ds 1979; 23:698-707.

Smith E J, Fadly A M, Crittenden L B. Observation on an enzyme-linked immunosorbent assay for the detection of antibodies against avian leukosis-sarcoma viruses. Avian Dis 1986; 30: 488-4493.

Smith E J Williams S M, Fadly A M. Detection of avian leukosis virus subgroup j using the polymerase chain reaction. Avian Dis 1998; 42: 375-380.

Smith L M, Brown S R, Howes K, McLeod S, Arshad S S, Barron G S, Venugopal K, McKay J C, Payne L N. Development and application of polymerase chain reaction (PCR) tests for the detection of subgroup J avian leukosis virus. Virus Res 1998; 54: 87-98.

As used herein, “subject” can mean a human or a non-human.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A method for detecting avian leukosis/sarcoma virus (ALSV) in a subject, comprising the steps of:

(a) isolating nucleic acid from a subject;

(b) subjecting said nucleic acid to a polymerase chain reaction (PCR) amplification using at least one primer set selected from the group consisting of

J1F (SEQ ID NO: 22)/J1R (SEQ ID NO: 24),

J1F (SEQ ID NO: 22)/J2R (SEQ ID NO: 25),

J2F (SEQ ID NO: 23)/J1R (SEQ ID NO: 24),

J2F (SEQ ID NO: 23)/J2R (SEQ ID NO: 25),

J1F (SEQ ID NO: 22)/J3R (SEQ ID NO: 26),

AL1D (SEQ ID NO: 1)/ALIVR1 (SEQ ID NO: 21),

ALIVF1 (SEQ ID NO: 20)/ALIVR1 (SEQ ID NO: 21), and

AL1D (SEQ ID NO: 1)/ALXB (SEQ ID NO: 19); and (c) detecting integrated ALSV by visualizing product or products of the PCR amplification.

2. The method of claim 1, wherein:

step (a) further includes obtaining a sample from the subject and processing the sample to isolate nucleic acid from the sample;

step (b) further includes examining the nucleic acid isolated from the sample to detect ALSV long terminal repeat nucleic acid sequences; and wherein the product or products are indicative for an increased potential of developing ALSV-induced cancer or infection.

3. The method of claim 1, wherein the nucleic acid from the subject is isolated from the group consisting of a tissue, cells, fluid sample, and a tumor.

4. The method of claim 1, wherein:

step (a) further includes obtaining a sample from the subject being a cancer patient and processing the sample to isolate nucleic acid;

step (b) further includes examining the nucleic acid isolated from the sample to detect ALSV long terminal repeat nucleic acid sequences; and wherein the product or products are indicative of the cancer patient having ALSV-induced cancer or infection.

5. The method of claim 4, wherein said cancer patient has a tumor selected from the group consisting of lung, liver, colon, esophagus, and hemopoietic/lymphatic tumors and the sample is obtained from the tumor.

6. The method of claim 1, wherein:

step (a) further includes obtaining a sample from the subject being a host and processing the sample to isolate nucleic acid of the host genome;

step (b) further includes examining the nucleic acid isolated from said sample to detect ALSV long terminal repeat nucleic acid sequences; and wherein the product or products indicate the presence of integrated ALSV in the host genome.

7. The method of claim 1, wherein the polymerase chain reaction amplification using at least one primer set detects ALSV long terminal repeat nucleic acid sequences.

8. The method of claim 1 further comprising the step of, prior to step (b), subjecting the nucleic acid to a polymerase chain reaction amplification using at least one primer set is selected from the group consisting of ALID (SEQ ID NO: 1)/AL2B (SEQ ID NO: 2), nprA181 (SEQ ID NO: 3)/nprA308 (SEQ ID NO: 4), nprA271 (SEQ ID NO: 5)/AL2B (SEQ ID NO: 2), RAVO-1 (SEQ ID NO: 6)/RAVO-2 (SEQ ID NO: 7), AL1D (SEQ ID NO: 1)/AAu (SEQ ID NO: 13), S-Au (SEQ ID NO: 12)/A-Au (SEQ ID NO: 13), nprA271 (SEQ ID NO: 5)/A-Au (SEQ ID NO: 13), Sn271J (SEQ ID NO: 14)/A-AuJ (SEQ ID NO: 15); J1F (SEQ ID NO: 22)/J1R (SEQ ID NO: 24), J1F (SEQ ID NO: 22)/J2R (SEQ ID NO: 25), J2F (SEQ ID NO: 23)/J1R (SEQ ID NO: 24), J2F (SEQ ID NO: 23)/J2R (SEQ ID NO: 25), J1F (SEQ ID NO: 22)/J3R (SEQ ID NO: 26), AL1D (SEQ ID NO: 1)/ALIVR1 (SEQ ID NO: 21), ALIVF1 (SEQ ID NO: 20)/ALIVR1 (SEQ ID NO: 21), AL1D (SEQ ID NO: 1)/NAL2B (SEQ ID NO: 18), ALIVF1 (SEQ ID NO: 20)/NAL2B (SEQ ID NO: 18), and AL1D (SEQ ID NO: 1)/ALXB (SEQ ID NO: 19).

9. The method of claim 1, wherein the PCR amplification of step (b) further comprises a plurality of PCR reaction rounds using at least a second primer set, different from the at least one primer set of claim 1, selected from the group consisting of J1F (SEQ ID NO: 22)/J1R (SEQ ID NO: 24), J1F (SEQ ID NO: 22)/J2R (SEQ ID NO: 25), J2F (SEQ ID NO: 23)/J1R (SEQ ID NO: 24), J2F (SEQ ID NO: 23)/J2R (SEQ ID NO: 25), J1F (SEQ ID NO: 22)/J3R (SEQ ID NO: 26), AL1D (SEQ ID NO: 1)/ALIVR1 (SEQ ID NO: 21), ALIVF1 (SEQ ID NO: 20)/ALIVR1 (SEQ ID NO: 21), AL1D (SEQ ID NO: 1)/NAL2B (SEQ ID NO: 18), ALIVF1 (SEQ ID NO: 20)/NAL2B (SEQ ID NO: 18), and AL1D (SEQ ID NO: 1)/ALXB (SEQ ID NO: 19).

10. A method for detecting integrated Subgroup J avian leukosis/sarcoma virus (ALSV) in a subject, comprising the steps of:

(a) isolating nucleic acid from a subject;

(b) subjecting said nucleic acid to a polymerase chain reaction (PCR) amplification using at least one primer set selected from the group consisting of:

J1F (SEQ ID NO: 22)/J1R (SEQ ID NO: 24),
J1F (SEQ ID NO: 22)/J2R (SEQ ID NO: 25),
J2F (SEQ ID NO: 23)/J1R (SEQ ID NO: 24),
J2F (SEQ ID NO: 23)/J2R (SEQ ID NO: 25),
J1F (SEQ ID NO: 22)/J3R (SEQ ID NO: 26),
AL1D (SEQ ID NO: 1)/ALIVR1 (SEQ ID NO: 21),
ALIVF1 (SEQ ID NO: 20)/ALIVR1 (SEQ ID NO: 21), and
AL1D (SEQ ID NO: 1)/ALXB (SEQ ID NO: 19); and (c) detecting integrated Subgroup J ALSV by visualizing product or products of the PCR amplification.

11. The method of claim 10, wherein:

step (a) further includes obtaining a sample from the subject and processing the sample to isolate nucleic acid from the sample;

step (b) further includes examining the nucleic acid isolated from the sample to detect Subgroup J ALSV long terminal repeat nucleic acid sequences; and wherein the product or products are indicative for an increased potential of developing Subgroup J ALSV-induced cancer or infection.

12. The method of claim 10, wherein the PCR amplification using at least one primer set detects Subgroup J ALSV long terminal repeat nucleic acid sequences.

13. The method of claim 10, wherein the nucleic acid from the subject is isolated from the group consisting of a tissue, cells, a tumor, and a fluid sample originating from the subject.

14. The method of claim 10, wherein the PCR amplification of step (b) further comprises a plurality of PCR reaction rounds using at least a second primer set, different from the at least one primer set of claim 10, selected from the group consisting of AL1D (SEQ ID NO:1)/AL2B (SEQ ID NO: 2), nprA181 (SEQ ID NO: 3)/nprA308 (SEQ ID NO: 4), nprA271 (SEQ ID NO: 5)/AL2B (SEQ ID NO: 2), RAVO-1 (SEQ ID NO: 6)/RAVO-2 (SEQ ID NO: 7), ALID (SEQ ID NO: 1)/A-Au (SEQ ID NO: 13), S-Au (SEQ ID NO: 12)/A-Au (SEQ ID NO: 13), nprA271 (SEQ ID NO: 5)/A-Au (SEQ ID NO: 13), Sn271J (SEQ ID NO: 14)/A-AuJ (SEQ ID NO: 15); J1F (SEQ ID NO: 22)/J1R (SEQ ID NO: 24), J1F (SEQ ID NO: 22)/J2R (SEQ ID NO: 25), J2F (SEQ ID NO: 23)/J1R (SEQ ID NO: 24), J2F (SEQ ID NO: 23)/J2R (SEQ ID NO: 25), J1F (SEQ ID NO: 22)/J3R (SEQ ID NO: 26), AL1D (SEQ ID NO: 1)/ALIVR1 (SEQ ID NO: 21), ALIVF1 (SEQ ID NO: 20)/ALIVR1 (SEQ ID NO: 21), AL1D (SEQ ID NO: 1)/NAL2B (SEQ ID NO: 18), ALIVF1 (SEQ ID NO: 20)/NAL2B (SEQ ID NO: 18), and AL1D (SEQ ID NO: 1)/ALXB (SEQ ID NO: 19).

15. The method of claim 14, wherein said PCR amplification is a touchdown PCR procedure.

16. The method of claim 10, wherein:

step (a) further includes obtaining a sample from the subject being a cancer patient and processing the sample to isolate nucleic acid;

step (b) further includes examining the nucleic acid isolated from the sample to detect the presence of Subgroup J ALSV long terminal repeat (LTR) nucleic acid sequences; and wherein the product or products are indicative of the cancer patient having Subgroup J ALSV-induced cancer or infection.

17. The method of claim 16, wherein said cancer patient has a tumor selected from the group consisting of lung, liver, colon, esophagus, and hemopoietic/lymphatic tumors and the sample is obtained from the tumor.

18. The method of claim 10, wherein:

step (a) further includes obtaining a sample from the subject being a host and processing the sample to isolate nucleic acid of the host genome;

step (b) further includes examining the nucleic acid isolated from the sample for the purpose of detecting the presence of Subgroup J ALSV long terminal repeat nucleic acid sequences; and wherein the product or products indicate the presence of integrated Subgroups J ALSV in the host genome.

19. The method of claim 10, wherein the at least one primer set is J1F (SEQ ID NO: 22)/J1R (SEQ ID NO: 24).

20. The method of claim 10, wherein the at least one primer set is J1F (SEQ ID NO: 22)/J2R (SEQ ID NO: 25).

21. The method of claim 10, wherein the at least one primer set is J2F (SEQ ID NO: 23)/J1R (SEQ ID NO: 24).

22. The method of claim 10, wherein the at least one primer set is J2F (SEQ ID NO: 23)/J2R (SEQ ID NO: 25).

23. The method of claim 10, wherein the at least one primer set is J1F (SEQ ID NO: 22)/J3R (SEQ ID NO: 26).

24. The method of claim 10, wherein the at least one primer set is AL1D (SEQ ID NO: 1)/ALIVR1 (SEQ ID NO: 21).

25. The method of claim 10, wherein the at least one primer set is ALIVF1 (SEQ ID NO: 20)/ALIVR1 (SEQ ID NO: 21).

26. The method of claim 10, wherein the at least one primer set is AL1D (SEQ ID NO: 1)/ALXB (SEQ ID NO: 19).

* * * * *

SEQUENCE LISTING

```
<160> NUMBER OF SEQ ID NOS: 26

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1

atcgtgcctt attaggaa                                                18


<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2

atgaagcctt ccgcttcat                                               19


<210> SEQ ID NO 3
<211> LENGTH: 24
```

-continued

<212> TYPE: DNA
<213> ORGANISM: Artificial Sequence
<220> FEATURE:
<223> OTHER INFORMATION: Primer

<400> SEQUENCE: 3
cagacgggtc taacatggat tgga 24

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
acccaggtgc acaccaatgt gg 22

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gccattttac cattcaccac 20

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
ccattttacc attcaccaca ttggt 25

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
atgaagcctt ctgcttcatt caggt 25

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
atcgggagag ttaaaaacct gggga 25

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
cggacctggg ggagagaccc tccct 25

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
atttttatta taaggcctgc tgaaa 25

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
atatgcatat taaaacaaga tttac 25

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ccacattggt gtgcacctgg gt 22

<210> SEQ ID NO 13
<211> LENGTH: 15
<212> TYPE: DNA
<213> ORGANISM: Artificial Sequence
<220> FEATURE:
<223> OTHER INFORMATION: Primer

<400> SEQUENCE: 13
agccttccgc ttcat 15

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gccattttac ctcccaccac 20

<210> SEQ ID NO 15
<211> LENGTH: 15
<212> TYPE: DNA
<213> ORGANISM: Artificial Sequence
<220> FEATURE:
<223> OTHER INFORMATION: Primer

<400> SEQUENCE: 15
agccatccgc ttcat 15

<210> SEQ ID NO 16
<211> LENGTH: 16
<212> TYPE: DNA
<213> ORGANISM: Artificial Sequence -continued
<220> FEATURE:
<223> OTHER INFORMATION: Primer

<400> SEQUENCE: 16
caccacattg gtgtgc 16

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
atgaagcctt ccgcttcat 19

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
atgaagcctt ctgcttcat 19

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
agccttctgc ttcatgca 18

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ggattggacg aaccactgaa tt 22

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
agggaatcaa cggtccggcc 20

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
gtaacgataa aacagcaa 18

-continued

```
<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23

tgtatttaag tgcctagc                                               18


<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24

gtcagggaat cgacggtccg gccatca                                     27


<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25

cggtccggcc atcaaccca                                              19


<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26

ggtaaaatgg cgtttattgt                                             20
```